(12) United States Patent
Tippey

(10) Patent No.: US 7,059,474 B2
(45) Date of Patent: *Jun. 13, 2006

(54) PACKAGED ARRAY OF FLEXIBLE ARTICLES

(75) Inventor: Darold Dean Tippey, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 355 days.

This patent is subject to a terminal disclaimer.

(21) Appl. No.: 10/349,120

(22) Filed: Jan. 22, 2003

(65) Prior Publication Data

US 2003/0155265 A1      Aug. 21, 2003

Related U.S. Application Data

(63) Continuation-in-part of application No. 09/435,759, filed on Nov. 8, 1999, now abandoned.

(51) Int. Cl.
*B65D 71/06* (2006.01)

(52) U.S. Cl. .................. 206/494; 206/499; 206/526

(58) Field of Classification Search ............... 206/494, 206/497, 499, 526; 604/385.1; 53/429, 53/438
See application file for complete search history.

(56) References Cited

U.S. PATENT DOCUMENTS

| 3,562,392 A | 2/1971 | Mylius ..................... 206/46 |
| 4,481,751 A | 11/1984 | Ujhelyi |
| 4,966,286 A | 10/1990 | Muckenfuhs ................ 206/610 |
| 4,998,929 A | 3/1991 | Bjöksund et al. ......... 604/385.2 |
| 5,036,978 A | 8/1991 | Frank et al. ................ 206/494 |
| 5,150,562 A | 9/1992 | Araki et al. |
| 5,163,558 A | 11/1992 | Palumbo et al. ............. 206/494 |
| 5,537,722 A | 7/1996 | Niederhofer et al. .......... 24/304 |
| 5,554,146 A | 9/1996 | Niederhofer et al. ....... 604/391 |
| 5,769,837 A | 6/1998 | Parr ........................... 604/390 |
| 5,934,470 A | 8/1999 | Bauer et al. ................. 206/494 |
| 5,971,153 A | 10/1999 | Bauer et al. ................. 206/494 |
| 6,079,562 A | 6/2000 | Bauer et al. ................. 206/494 |
| 6,425,227 B1 | 7/2002 | Salm et al. |
| 6,761,013 B1 * | 7/2004 | Tippey et al. ................. 53/429 |

FOREIGN PATENT DOCUMENTS

| DE | 26 14 235 A1 | 10/1977 |
| EP | 0 391 460 A1 | 10/1990 |
| EP | 0 618 148 A1 | 10/1994 |
| EP | 0 780 325 A1 | 6/1997 |
| WO | WO 97/23391 A1 | 7/1997 |

* cited by examiner

*Primary Examiner*—Bryon P. Gehman
(74) *Attorney, Agent, or Firm*—Dority & Manning, P.A.

(57) ABSTRACT

A novel packaging article and method are disclosed for an array of flexible, absorbent articles compressed or uncompressed, having an article front face, an article back face, an article top face, an article bottom face, and a pair of article side faces. An upper article section and a lower article section have mutually different calipers. The flexible, absorbent articles are placed in a configuration array such that article front faces contact article front faces or such that article back faces contact back faces of adjacent absorbent articles. The package provides an array having preferred size and requires less compressibility force. A flexible outer casing does not require compressing wrapping to maintain the array as previously required in conventional packaging arrays having a flexible outer casing. The packaging article and method are particularly suited for providing preferred advantages to the packaging and commercial distribution of disposable diapers.

31 Claims, 13 Drawing Sheets

PACKAGED ARRAY OF FLEXIBLE ARTICLES

This application is a continuation-in-part of prior co-pending U.S. Patent Application Ser. No. 09/435,759, filed Nov. 8, 1999 now abandoned.

BACKGROUND OF THE INVENTION

1. Technical Field

This invention relates to packaging a plurality of disposable articles. In one aspect, this invention relates to an article and method for packaging flexible disposable absorbent articles, including disposable diapers, underpants, guards-for-men garments, sanitary napkins, incontinence pads, undergarments, or briefs.

2. Background

Packaged product users and their purchasing motivations are sensitive to product package appearance and product cost.

Packaged product user's purchasing decisions reflect their sensitivities.

Producers of packaged consumer products are sensitive to sales volume and product and material costs and handling, shipping, and display costs. Producers of packaged consumer products, such as packaged absorbent articles, prefer to hold packaging production and material costs to a minimum. Producers have trade off decisions to make to balance the packaging appeal to the customer with a lowest cost of packaging materials and production costs associated with each packaging design.

Product and material costs, handling costs, shipping, and display costs not only affect packaging users and purchasing decisions, but also handling, shipping, and display space costs constrain further the design, configuration, and selection of the preferred packaging and product to be packaged.

INTRODUCTION TO THE INVENTION

During packaging, a variation or variations within the packaging in the arrangement of a plurality of flexible absorbent articles, e.g., in case carton packages of disposable diapers, have been found to make for flexible outer casings which are not filled completely. A region or regions of an array of the articles compress in a variable amount, depending on the element in the region, e.g., such as elastic elements including waist bands, standup cuffs, and elasticized side panels; or such as mechanical fasteners; or such as absorbent cores in absorbent products. Compression can damage the articles and can diminish end-use performance of the flexible disposable articles.

When flexible disposable absorbent articles including disposable diapers are packaged and compressed, the volume size differences or changes lead to "wedge-like" shaped packaging and to articles popping out of the outer casing at an inopportune time or in an undesired manner, e.g., two or three at a time. Special configurations of the articles within the outer casing distribute the mass or bulk of the absorbent articles. However, configurations reduce the speed of packaging and reduce the speed of production. The difference in caliper of the different parts of the absorbent articles leads to unstable and easily deformable packages. The shipment, storage, and display of unstable packages cause a variety of problems and difficulties, and the problems are more severe in compressed packaging.

An array of compressed flexible articles has one or more unit packages maintained in a packaged configuration by a paper or plastic wrapping. The whole array is encircled in a flexible covering made from a wrapping paper band of a film of a thermoplastic material. A package unit uses a configuration of the flexible articles folded and packed in a "head-to-tail", configuration. Individual paper wrappers maintain the array. Consumers tear open the outer plastic flexible covering and remove the inner paper or plastic wrappers placed across the width of the products.

It is an object of the present invention to provide a package including an array of flexible compressed articles.

It is an object of the present invention to provide a package including an array of flexible compressed articles and also make efficient use of an available packaging volume, redistributing an orientation of flexible articles before packaging.

It is an object of the present invention to compress the packaging to a relatively small volume without causing damage or significant reduction in the performance of the articles, especially absorbent articles.

It is an object of the present invention to enhance the free space inside an outer casing and shipping unit for corrugated cases and preferred pallet usage.

It is an object of the present invention to provide a stable and uniform shape in the nature of a rectangular, square, or designated design for a preferred fit when the package is shipped, stored, and displayed and further provide for a preferred appearance.

It is an object of the present invention to provide preferred consumer access to the absorbent articles contained within the flexible outer casing when the outer casing is opened.

It is an object of the present invention to provide preferred removal of a single absorbent article for use and when withdrawn from the package.

It is an object of the present invention to eliminate inner shapes, wrappers, or compression as a necessary means for maintaining a certain configuration of the articles.

It is an object of the present invention to reduce material and shipping costs and allow more absorbent articles in smaller packages.

It is an object of the present invention to distribute compression forces uniformly across the package, eliminating distinct high and low compression areas within the package.

It is an object of the present invention to provide a preferred process for placing the articles in the package.

It is an object of the present invention further to provide a simple and reliable method for the compressed packaging of an array of flexible articles while maintaining and increasing the speed and efficiencies of production.

These and other preferred features and objects of the present invention will become apparent from the detailed description of the specification in conjunction with the figures of the drawings which follow.

SUMMARY OF THE INVENTION

The package and method in accordance with the present invention provide means and method for novel packaging which contains an array of flexible articles, each article having an article front face, an article back face, an article top face, an article bottom face, article side faces, an upper article section and a lower article section, the article sections having mutually different caliper; wherein each article in contact with another article is placed with an article front face in contact with an article front face or wherein each article in contact with another article is placed with an article back face in contact with an article back face; the array having a first array region and a second array region, the upper and lower article sections being distributed over the first and second array regions of the array, wherein the upper and lower article sections are distributed such that a reordered size difference of the first and second array regions is at least about 10% smaller than when all of the upper article sections are located in the same array region of the array.

The mutually different caliper of the article sections consists of a caliper in the upper article section different from the lower article section. The package contains no compressing paper wrapping required to maintain the array of the article.

The upper and lower article sections are distributed such that the sizes of the first and second array regions of the array are substantially equal. In one aspect, each article in contact with another article is placed with the article bottom faces in a contact with an interfacial plane with the top faces of adjacent articles. In one aspect, the reordered size difference is at least about 15% smaller. The dimension of the first array region of the array is substantially equal to the dimension of the second array region of the array. The mutually different caliper of the article sections consists of a caliper in the upper article section different from the lower article section.

The package in accordance with the present invention includes a flexible outer casing containing an array of compressed, flexible absorbent articles, each article including an article front face, an article back face, an article top face, an article bottom face, article side faces, an upper article section and a lower article section, the article sections having mutually different compressibilities and calipers; wherein at least a portion of the absorbent articles are placed with the article front faces in a contacting relationship and at least a portion of the absorbent articles are placed with the article back faces in a contacting relationship; the array having a first array region and a second array region and the upper and lower article sections of each articles being distributed over the first and second array regions of the array; wherein the distribution of the upper and lower article sections is such that the difference in the compression force for compression of the first and second array regions to between 0% and 90% of an uncompressed volume is at least 10% smaller than the difference in the compression force for compression of the first and second array regions when all of the upper article sections of each articles are located in the same array region of the array; and the flexible outer casing maintains the array of compressed articles.

The upper and lower article sections are distributed in such a way that the compression forces for the first and second array regions of the array are substantially equal. The article bottom faces in a contacting relationship form a reoccurring stack pattern with the article top faces of adjacent articles. The orientation of each articles is periodically alternated. After compression, the dimension along the direction of compression of the first array region of the array is equal to the dimension along the direction of compression of the second array region of the array. After compression, the expansion force of the first array region is equal to the expansion force of the second array region. The absorbent articles consist of different caliper in the upper and lower article sections. The absorbent articles consist of different caliper in the upper and lower article sections.

The package in accordance with the present invention includes an array of disposable diapers, the disposable diapers including a diaper front face, a diaper back face, a diaper top face, a diaper bottom face, diaper side faces, an upper diaper section and a lower diaper section, the diaper sections having mutually different calipers, wherein at least a portion of the disposable diapers are placed with the diaper front faces in a contacting relationship and at least a portion of the diaper back faces in a contacting relationship; further including a flexible outer casing; the array having a first array region and a second array region and the upper and lower diaper sections of the disposable diapers being distributed over the first and second array regions of the array, wherein the distribution of upper and lower diaper sections is such that the difference in size of the first and second array regions is at least about 10% smaller than when all of the upper diaper sections of the absorbent disposable diapers are located in the same array region of the array.

The upper and lower diaper sections of the disposable diapers are distributed such that the sizes of the first and second array regions of the array are substantially equal. At least a portion of the disposable diapers are placed with the diaper bottom faces in a contacting relationship forming a reoccurring stack pattern with the top faces of adjacent disposable diapers. The orientation of the disposable diapers is periodically alternated. The dimensions of the first array region of the array are equal to the dimensions of the second array region of the array. The disposable diapers consist of different calipers in the upper and lower diaper sections. The package does not contain compressing wrapping required to maintain the array of the disposable diapers.

The package in accordance with the present invention contains an array of compressed, flexible disposable diapers, the disposable diapers including a diaper front face, a diaper back face, a diaper top face, a diaper bottom face, diaper side faces, an upper diaper section and a lower diaper section, the diaper sections having mutually different compressibilities and calipers; wherein at least a portion of the disposable diapers are placed with the disposable front faces in contacting relationship and at least a portion of the diaper back faces in contacting relationship; further including a flexible outer casing; the array having a first array region and a second array region and the upper and lower diaper sections of the disposable diapers being distributed over the first and second array regions of the array, wherein the distribution of the upper and lower diaper sections is such that the difference in the compression force for compression of the first and second array regions to between 0% and 90% of an uncompressed volume is at least 10% smaller than the force for compression of the first and second array regions when all of the upper diaper sections of the disposable diapers are located in the same array region of the array; and the flexible outer casing maintains the array of the compressed disposable diapers.

The upper and lower diaper sections of the disposable diapers are distributed in such a way that the compression forces for the first and second array regions of the array are substantially equal. At least a portion of the disposable diapers are placed with the diaper bottom faces in contacting relationship forming a reoccurring stack pattern with the top faces of adjacent disposable diapers. The orientation of the disposable diapers is periodically alternated. The dimension along the direction of compression of the first array region of the array is equal to the dimension along the direction of compression of the second array region of the array. After compression, the expansion force of the first array region is equal to the expansion force of the second array region. The disposable diapers consist of different calipers in the upper and lower diaper sections. The package does not require compressing wrapping to maintain the array of the compressed disposable diapers.

The method in accordance with the present invention forms a package, including transporting a plurality of articles in a consecutive manner to a folding unit, folding each article, changing the orientation of each article at regularly spaced intervals, aligning a predetermined number of each article with an article front face or an article back face in a contacting relationship such that the article front face contacts another front face or an article back face contacts an article back face of an adjacent article to form an uncompressed array. A predetermined number of each articles have an upper article section located in a first array region of the array and a second predetermined number of each articles have an upper article sections located in a second array region of the array. The method includes placing the array in a flexible outer casing.

The method in accordance with the present invention forms a package, including the following steps of transporting a plurality of flexible, absorbent articles in a consecutive manner to a folding unit; folding each flexible, absorbent article; changing the orientation of each flexible, absorbent article at regularly spaced intervals; aligning a predetermined number of each flexible, absorbent articles in adjacent contact to have an article front face in contact with an article front face or an article back face in contact with an article back face to form an uncompressed array, wherein a predetermined number of each flexible, absorbent articles have an the upper article section located in a first array region of the array; compressing the array; and placing the compressed array in a flexible outer casing.

A second predetermined number of each flexible, absorbent article have an upper article section located in a second array region of the array.

The method in accordance with the present invention forms a package, including transporting disposable diapers in a consecutive manner to a folding unit; folding each disposable diaper; changing the orientation of the disposable diapers at regularly spaced intervals; aligning a predetermined number of the disposable diapers with a diaper front face or a diaper back face in a contacting relationship such that front faces contact front faces or back faces contact back faces to form an uncompressed array, wherein a predetermined number of the disposable diapers have an upper diaper section located in a first array region of the array and a second predetermined number of the articles have an upper article section located in a second array region of the array; compressing the array; and placing the compressed array in a flexible outer casing.

The compression force is substantially uniform across the first and second array regions.

The method in accordance with the present invention forms a package, including the following steps of transporting disposable diapers in a consecutive manner to a folding unit; folding the disposable diapers; and changing the orientation of the disposable diapers at regularly spaced intervals.

The method in accordance with the present invention forms a package, including the following steps of transporting disposable diapers in a consecutive manner to a folding unit; folding each disposable diaper individually; changing the orientation of the disposable diapers at regularly spaced intervals; aligning a predetermined number of the disposable diapers with a diaper front face in a contacting relationship or a diaper back face in a contacting relationship to form an uncompressed array, wherein a predetermined number of the disposable diapers have an upper diaper section located in a first array region of the array, compressing the array; and placing the compressed array in a flexible outer casing.

A second predetermined number of the disposable diapers have an upper diaper section located in a second array region of the array.

The method in accordance with the present invention forms a package by transporting disposable diapers in a consecutive manner to a folding unit; folding each of the disposable diapers individually; changing the orientation of the disposable diapers at regularly spaced intervals; aligning a predetermined number of the disposable diapers with diaper front faces or diaper back faces in a contacting relationship to form an uncompressed array, wherein a predetermined number of the disposable diapers have an upper diaper section located in a first array region of the array and a second predetermined number of the disposable diapers have an upper diaper section located in a second array region of the array; compressing the array; placing the compressed array in a flexible outer casing; and wherein the compression force is substantially uniform across the first and second array regions.

DETAILED DESCRIPTION

Figure 1:
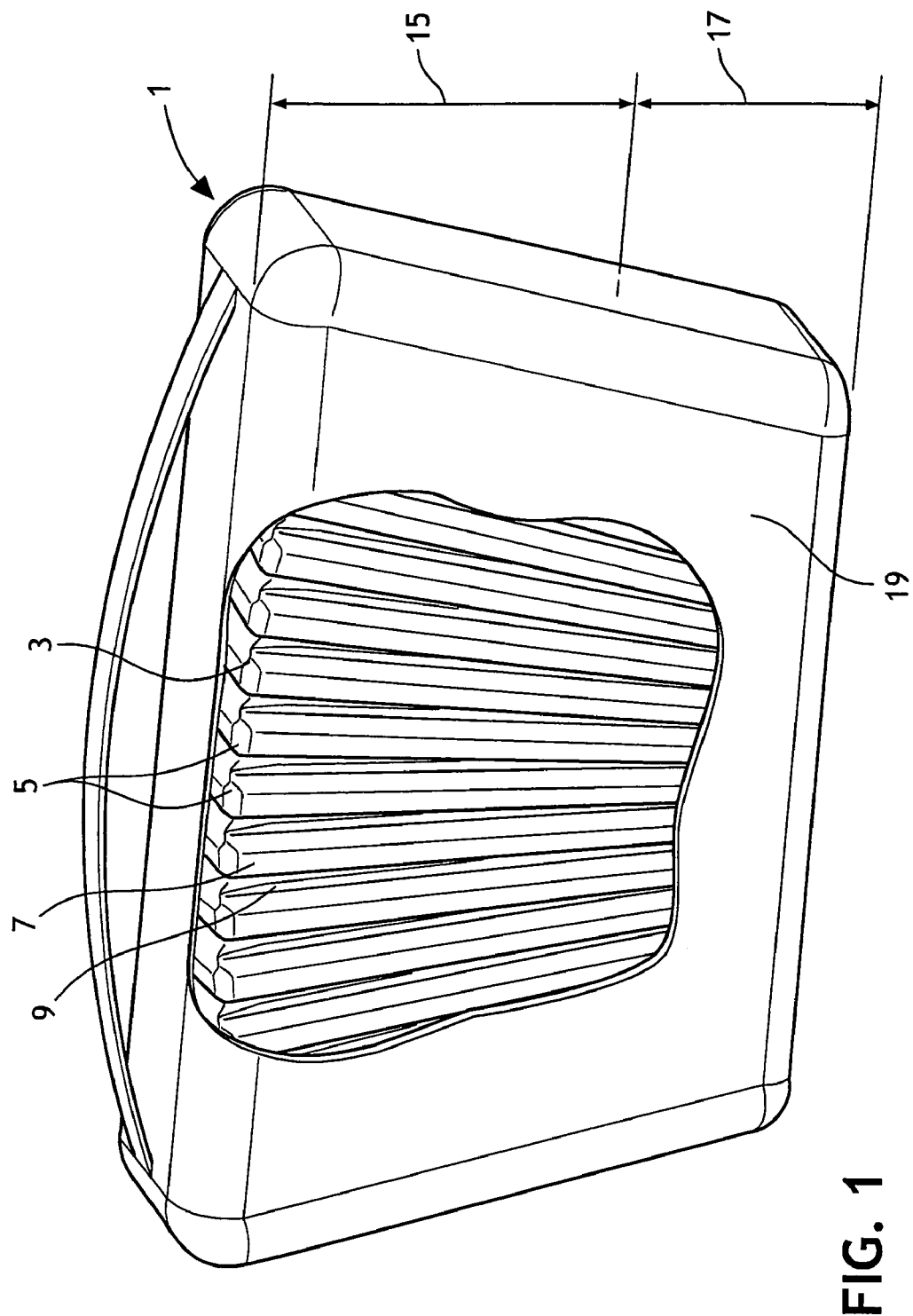
FIG. 1 shows a perspective view of a package including an array of flexible articles, such as absorbent articles in a uniformly stacked product.

The packaging article and method of the present invention include a flexible outer casing and absorbent articles arranged within the outer casing and placed in an array such that at least a portion of article front faces are in a contacting relationship. The present invention provides a package, article, and method including an array of flexible articles housed in a regions, namely, a first region and a second region. Each article has an article top face, a bottom face, a front face, a back face, and a pair of side faces distributed over the first and second region of the array of articles. The top, front, back, and side faces of the article are referred to as the upper section, and the bottom, front, back, and side faces of the article are referred to as the lower section. The upper and lower sections have mutually different calipers, wherein caliper means thickness or bulk.

The flexible, disposable article packaging and method of the present invention provide a package including an array of flexible compressed articles.

The flexible, disposable article packaging and method of the present invention provide a package including an array of flexible compressed articles and also make efficient use of an available packaging volume, redistributing an orientation of flexible articles before packaging.

The flexible, disposable article packaging and method of the present invention compress the packaging to a relatively small volume without causing damage or significant reduction in the performance of the articles, especially absorbent articles.

The flexible, disposable article packaging and method of the present invention enhance the free space inside an outer casing and shipping unit for corrugated cases and preferred pallet usage.

The flexible disposable article packaging and method of the present invention provide a stable and uniform shape in the nature of a rectangular, square, or designated design for a preferred fit when the package is shipped, stored, and displayed and further provide for a preferred appearance.

The flexible disposable article packaging and method of the present invention provide preferred consumer access to the absorbent articles contained within the flexible outer casing when the outer casing is opened.

The flexible disposable article packaging and method of the present invention provide preferred removal of a single absorbent article for use and when withdrawn from the package.

The flexible disposable article packaging and method of the present invention eliminate inner shapes, wrappers, or compression as a necessary means for maintaining a certain configuration of the articles.

The flexible disposable article packaging and method of the present invention reduce material and shipping costs and allow more absorbent articles in smaller packages.

The flexible disposable article packaging and method of the present invention distribute compression forces uniformly across the package, eliminating distinct high and low compression areas within the package.

The flexible disposable article and method of the present invention provide a preferred process for placing the articles in the package.

The flexible disposable article packaging and method of the present invention further provide a simple and reliable method for the compressed packaging of an array of flexible articles while maintaining and increasing the speed and efficiencies of production.

Conventional packaging processes align the absorbent articles in an array wherein the back face of a first article is in a contacting relationship with the front face of an adjacent article, and the bottom face of the first article is adjacent the bottom face of the adjacent article. According to the configuration of articles within the array of present invention, at least a portion or a predetermined number of articles within the array are in a front face to front face contacting relationship with adjacent articles, or, alternatively, in a back face to back face contacting relationship. At least a portion or a predetermined number of the articles within the array are in a top face to bottom face relationship with adjacent articles. The articles in a front face to front face contacting relationship with adjacent articles, or, alternatively, in a back face to back face contacting relationship are the articles in the top face to bottom face relationship with adjacent articles.

The differences in the sizes or the compression forces of the first and second regions when the upper and lower sections are distributed throughout the array of articles are at least 10% smaller than the differences in the sizes of the articles (or the compression forces for compression of the articles when compressed packaging is being utilized) of the largest region when all the upper sections of the articles are located in the same region of the array of the articles. When a compression force is applied to the articles, the articles are compressed to between about 10% to about 75% of their uncompressed volume.

By redistributing the orientation or configuration of the articles within the array before packaging, the packaging of the array of the articles becomes uniform. In operations where compressed packaging is utilized, the array of articles is reoriented before compression force is applied. While not necessary to reorient the articles within the array before compression force is applied to the array, the array of articles is more stable for processing when the array is reoriented prior to the compression. The differences in the sizes of the upper and lower sections of the articles in the reoriented array is reduced to obtain an equal distribution of the articles or volume of the first and second regions.

Reorientation provides for a preferred use of volume or space within the outer casing. Reorientation prevents over-compression of various parts of the articles where compressed packaging is utilized. Reorientation reduces or prevents damage to the absorbent articles.

It has been found that a tendency for the articles to pop out of the outer casing during handling is reduced by the packaging article and method of the present invention.

Using the reoriented configuration in the packaging of the present invention for the array of articles, more articles are included in a single array before the array becomes unstable. In this way, the packaging process is simplified, and the speed of the production of the articles is maintained or increased while providing more a stable product package having the preferred advantages of the flexible disposable article and method of the present invention.

It has been found that preferred load bearing properties and shape stability of the package is provided by the flexible disposable article and method of the present invention. The packages of an reoriented array of absorbent articles are stacked in a stable manner for shipping, handling, and display.

It has been found that a package according to the present invention can be compressed by a compression at least 10% higher in the direction of compression in comparison to a package having an equal number of articles wherein all the upper sections are located in the same region of the array of the articles.

In one embodiment of the packaging in accordance to the present invention, the articles are distributed within the array such that the sizes are substantially equal or the compression forces are substantially equal when compressed packaging is utilized for the first and second regions of the array of the articles.

In this way, the packaging apparatus of the present invention accommodates a variety of bag sizes. In the case when compressed packaging is utilized, the compression apparatus pivoting preventive support for the compression plates accommodates different reduced compressibilities of the array of articles.

Alternatively, the array of the absorbent articles is orientated such that after compression the expansion forces of the first region of the array are substantially equal to the expansion force of the second region to counter deformation of the package on removal of the compression forces.

Arrays of articles are formed by stacking bi-folded absorbent articles, such as diapers, together, having either non-uniform caliper or low and high density regions. A bi-folded diaper is folded once on itself at its crotch region. Such bi-folded diapers have a rounded upper section having high compression resistance which corresponds to the crotch region of the unfolded diaper, and a lower section with low compression resistance, which corresponds to the waist regions of the unfolded diaper. The preferred maximum packaging of the present invention is achieved when the orientation of rounded upper sections is alternated within the array of the absorbent articles. The orientation of the upper sections is alternated for groups of two or more articles, and the number of rounded upper sections in the first and second regions of the array of compressed diapers need not necessarily be equal. Articles, such as absorbent articles, are tri-folded, bi-tri-folded, or folded by any of a variety of folds.

Compressibility reduces the volume when the predetermined force is applied to the article or to the array of articles, particularly absorbent articles. Reduction in volume is between 20% and 70% of the uncompressed volume for the packaging article and method of the present invention.

The present invention includes a packaged array of flexible articles housed in a flexible outer casing. In one aspect, an array of absorbent articles has two regions, viz., a first region and a second region. Each article provides a top face, a bottom face, a front face, a back face, and a pair of side faces distributed over the first and second region of the array of articles. An upper section and a lower section have mutually different calipers, wherein by caliper is meant thickness or bulk.

Conversely to packaging processes wherein absorbent articles are aligned in an array having a back face of one article in contacting relationship with a front face of an adjacent article, and a bottom face of a first article adjacent a bottom face of an adjacent article, according to the configuration of articles within the array of present invention at least a portion or a predetermined number of articles within the array are in a front face to front face contacting relationship with adjacent articles or alternatively in a back face to back face contacting relationship. At least a portion or a predetermined number of articles within the array are in a top face to bottom face relationship with adjacent articles. The articles in a front face to front face contacting relationship with adjacent articles or alternatively in a back face to back face contacting relationship are separated from the articles in the top face to bottom face relationship with the adjacent articles.

The differences in the sizes or the compression forces for compression of absorbent articles, for compressed packaging of the first and second regions when the upper and lower sections are distributed throughout the array of articles, are at least 10% smaller than the differences in the sizes of the articles or the compression forces for compression of the articles when compressed packaging is utilized of the largest region when all the upper sections of the articles are located in the same region of the array of the articles. When a compression force is applied to the articles, the articles preferably are compressed to between about 10% to about 75% of an uncompressed volume.

Reorientation provides for a preferred use of volume or space within the outer casing. Reorientation prevents over-compression of various parts of the articles when compressed packaging is utilized. Reorientation reduces or prevents damage to absorbent articles and eliminates a tendency for the articles to pop out of the outer casing during handling is reduced.

Using the reoriented configuration of the present invention for the array of articles, a higher number of articles are included in a single array before the array becomes unstable. In this way, the packaging process is simplified, and the speed of the production of the articles is increased while providing a more stable product package having the advantages of the present invention.

Load bearing properties and shape stability of the package are increased. The reoriented array of absorbent articles is stacked in a more stable manner for shipping, handling, and display.

It has been found that a package according to the present invention provides a plurality of articles compressed by at least 10% more in the direction of compression in comparison to a package of an equal number of articles wherein all the upper sections are located in the same region of the array of the articles.

In one embodiment of a packaging operation according to the present invention, the articles to be packaged are distributed within an array such that the sizes or the compression forces for the first and second regions of the array of the articles are equal. In this way, the packaging apparatus accommodates the need for a variety of bag sizes. When compressed packaging is used, the compression apparatus is simplified as the pivoting preventive support for the compression plates to accommodate the different compressibilities of the array of articles is reduced.

The array of the absorbent articles is oriented such that after compression the expansion force of the first region of the array is equal to the expansion force of the second region to counteract deformation of the package during removal of the compression forces.

An array of articles is formed by stacking bi-folded absorbent articles, e.g., diapers, together having either non-uniform calipers or having low and high density regions. In one aspect, a bi-folded diaper is folded once on itself at its crotch region.

Bi-folded diapers have a rounded upper section and a high compression resistance corresponding to the crotch region of the unfolded diaper and a lower section with a low compression resistance corresponding to the waist regions of the unfolded diaper.

The packaging advantage of the present invention is provided when the orientation of the rounded upper sections is alternated within the array of the absorbent articles. The orientation of the upper sections is alternated for groups of two or more articles, and the number of rounded upper sections in the first and second regions of the array of compressed diapers is not equal. In one aspect, absorbent articles are tri-folded or bi-tri-folded.

Compressibility reduces the volume when the predetermined force is applied to the article or to the array of absorbent articles.

It has been found that the packaging article and method of the present invention reduce volume between 20% and 70% of the uncompressed volume.

A further detailed understanding of the packaging article and method of the present invention will be achieved by reference to the detailed description which follows in conjunction with the study of the attached figures of the drawings.

Figure 2:
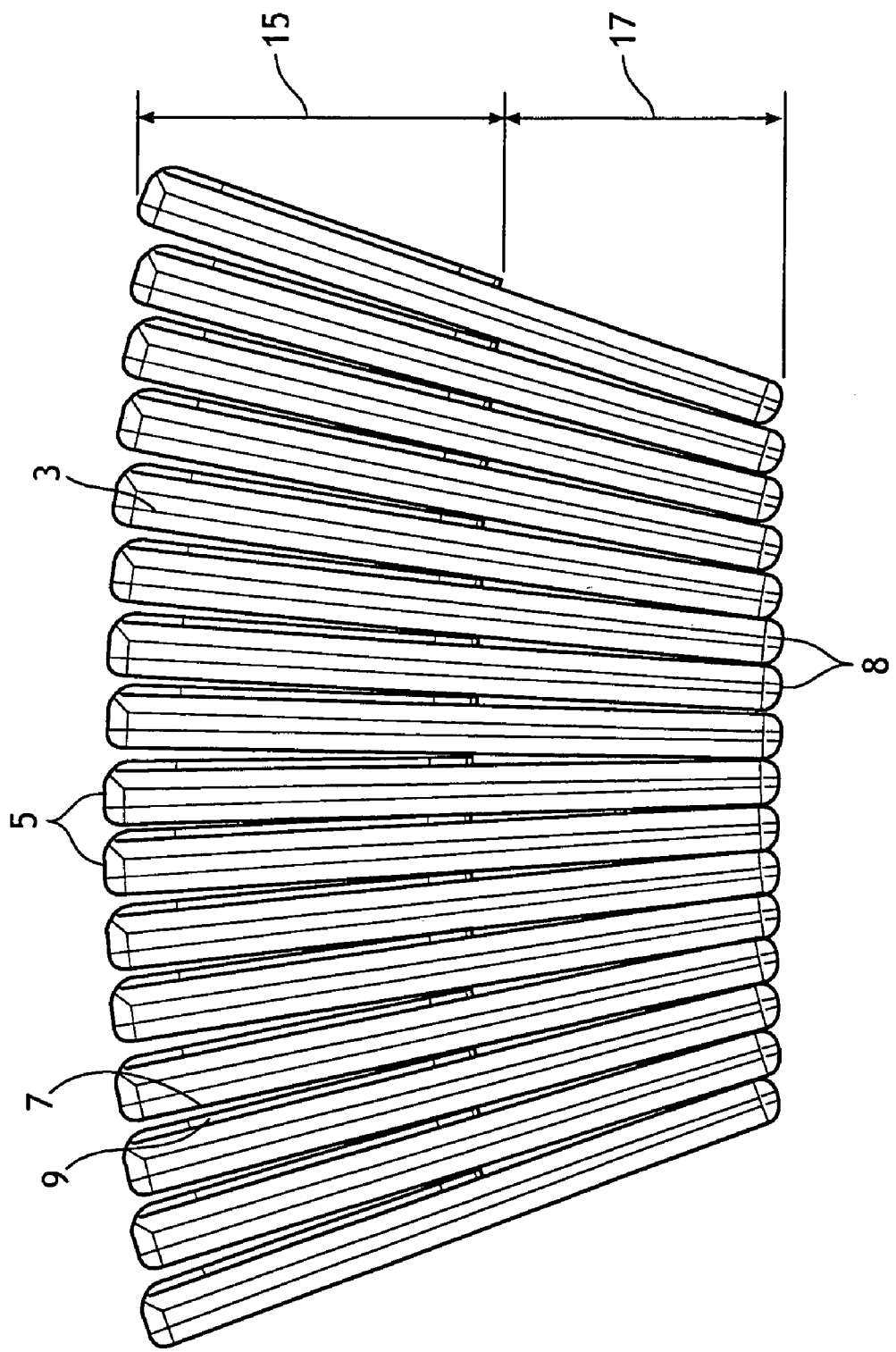
FIG. 2 shows a perspective view of folded articles having upper and lower sections of similar compressibilities or caliper in a uniformly stacked product.

Referring now to FIG. 1 and FIG. 2, a package 1 contains an array 3 of folded, flexible articles 5, such as absorbent articles. The array 3 has a first region 15 and a second region 17. In one aspect, the articles 5 are compressed within the package 1. The articles 5 include diapers, underpants, undergarments, guards-for-men garments, sanitary napkins, incontinence pads, other absorbent article, or clothing, gowns, medical drapes, masks, or protective coverings.

When compressed, the articles 5, e.g., absorbent articles, are compressed to between about 0% and about 90% of an uncompressed volume, preferably about 0% and about 80%, more preferably about 10% and 75%, and most preferably about 20% and 70% of uncompressed volume. The articles 5 are contained within a flexible outer casing 19, with portions of the structure of the flexible outer casing 19 being cut away in FIG. 1 to show more clearly the array 3 of the articles 5, in this case absorbent articles, within the package 1. The flexible outer casing 19 maintains the array 3 of articles 5, compressed or otherwise, and includes a thermoplastic bag or other flexible packaging material.

In conventional or standard packaging processes, the articles 5 are aligned in an array 3 wherein the back face 9 of one article 5 is in a contacting relationship with the front face 7 of the adjacent article 5, and the bottom face 8 of the first article 5 is adjacent the bottom face 8 of the adjacent article 5.

According to the configuration of articles 5, such as absorbent articles, within the array 3 of the package 1 of the present invention, at least a portion or a predetermined number of articles 5 within the array 3 are in a front face 7 to front face 7 contacting relationship with adjacent articles 5, or alternatively, in a back face 9 to back face 9 contacting relationship. In addition, at least a portion or a predetermined number of the articles 5 within the array 3 are in a top face 3 to bottom face 8 relationship with adjacent articles 5. The two portions of articles 5 may or may not be the same articles 5.

Figure 3:
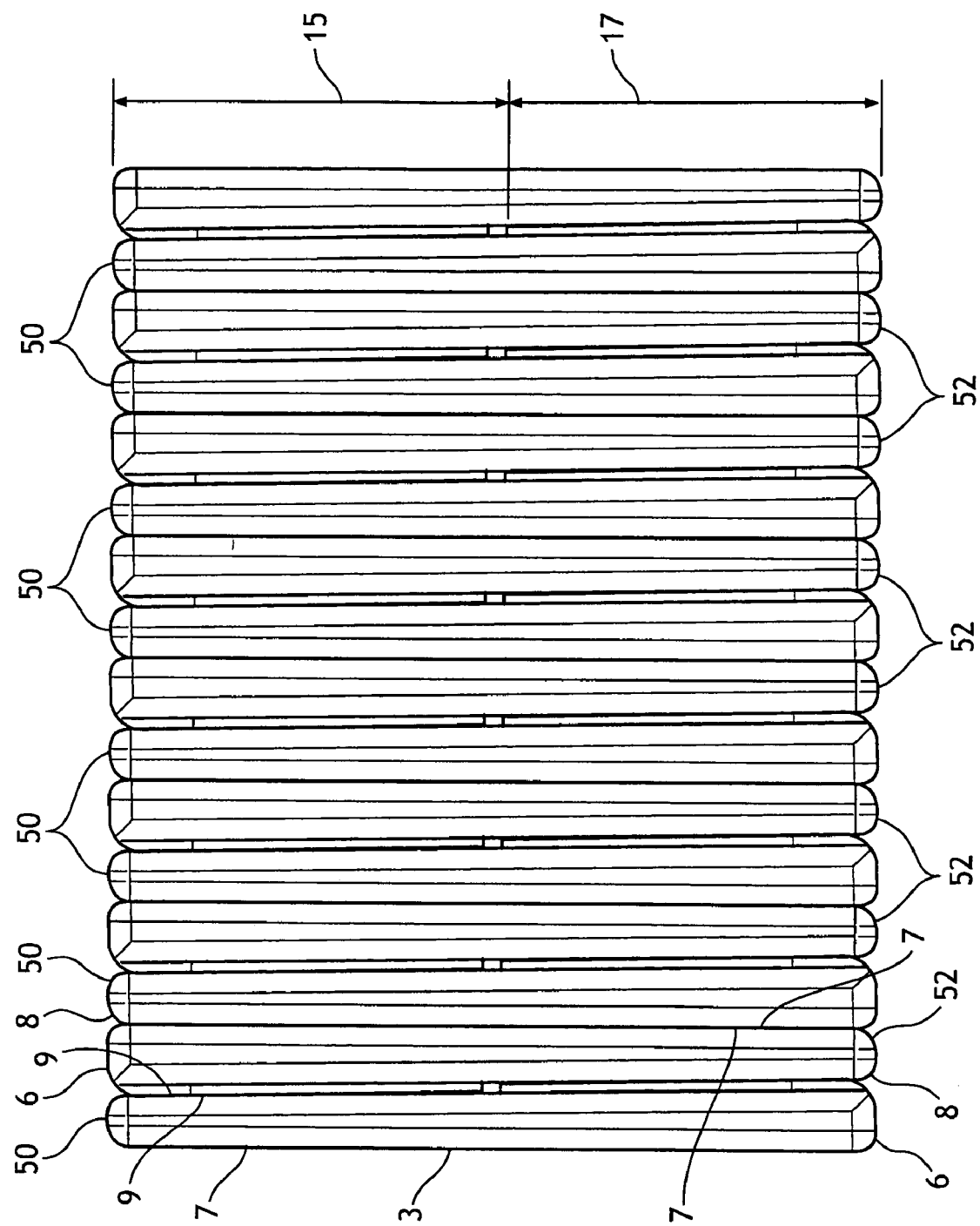
FIG. 3 shows a perspective view of folded articles, such as absorbent articles, having upper and lower sections of different compressibilities or caliper in an alternatively stacked product.
Figure 4:
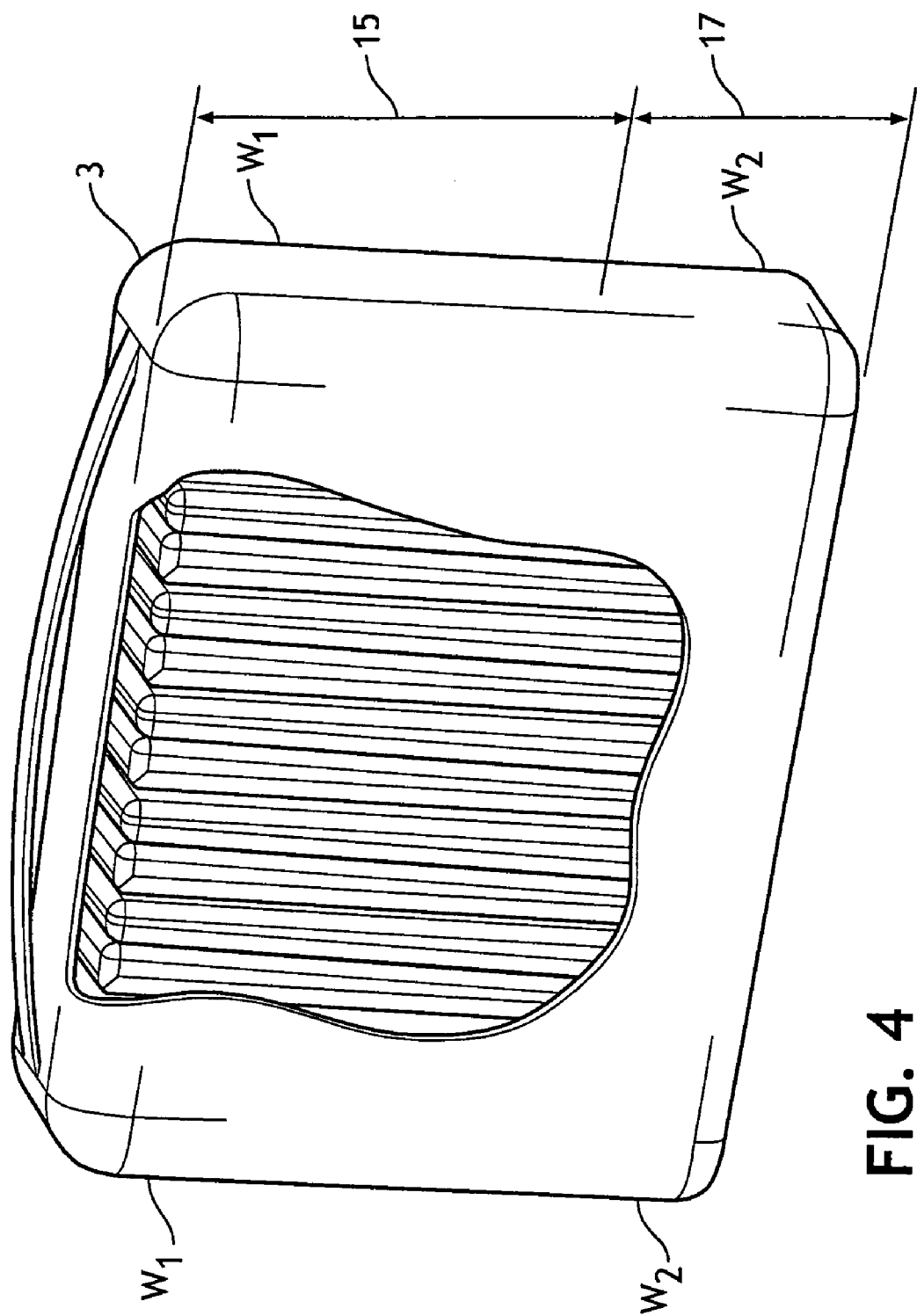
FIG. 4 shows a perspective view of folded articles, such as absorbent articles, having upper and lower sections of different compressibilities or caliper in an alternatively stacked product.

Referring now to FIG. 3 and FIG. 4, a preferred orientation is shown of articles 50 and 52, absorbent or otherwise, according to the present invention. The number of upper sections 11 and lower sections shown in FIG. 5 of the articles 50 and 52 in the first region 15 of the array 3 is either equal to the number of upper sections 11 and lower sections 13 of the articles 50 and 52 in the second region 17 of the array 3, or it differs by one. In this way, the compression force W1 necessary to compress the first region 15 is substantially equal to the compression force W2 required to compress the second region 17 of the array 3, wherein W1≈W2.

Preferably, according to the present invention, the articles 5 in a front face 7 to front face 7 contacting relationship with adjacent articles 5, or alternatively, in a back face 9 to back face 9 contacting relationship, are the articles 5 in the top face 6 to bottom face 8 relationship with the adjacent articles 5. In such a configuration, the articles 5 in the front face 7 to front face 7 contacting relationship with adjacent articles 5, or alternatively, in a back face 9 to back face 9 contacting relationship, also would be the articles 5 within the array 3 in a top face 6 to bottom face 8 relationship with adjacent articles 5. Accordingly, the article and method of present invention is shown in FIG. 3.

However, the articles 5 in the front face 7 to front face 7 contacting relationship with adjacent articles 5 or, alternatively, in a back face 9 to back face 9 contacting relationship are not required to be the articles 5 within the array 3 in a top face 6 to bottom face 8 relationship with adjacent articles 5.

Between 5 and 100 absorbent articles 5 preferably are contained in the array 3. When the articles 5 are not absorbent articles, between 3 and 1000 articles 5 preferably are contained in the array 3.

Figure 5:
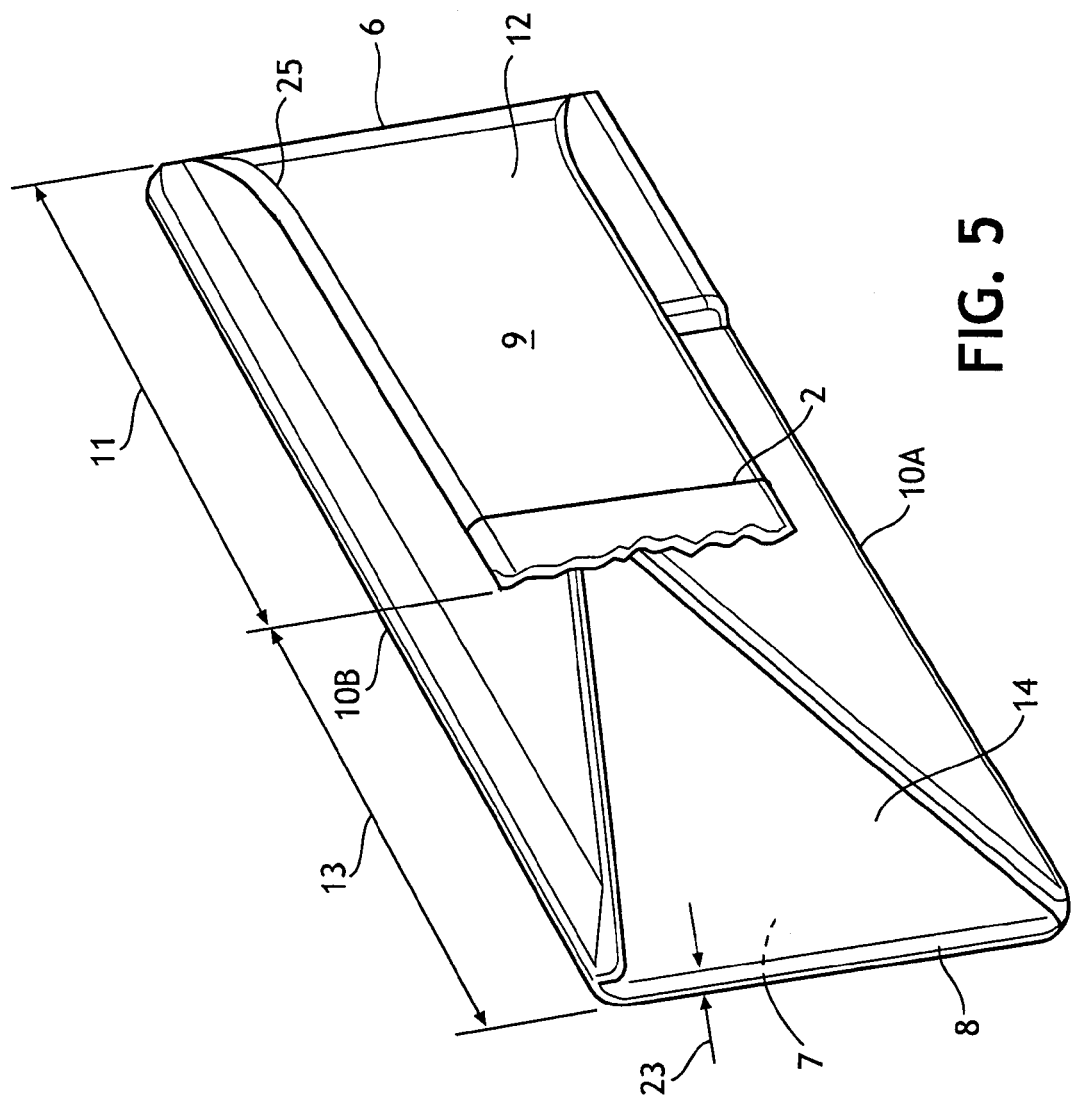
FIG. 5 shows a perspective view of a folded absorbent article, having a front face hidden in a completely folded back view.

Referring now to FIG. 5, each folded article 5 has a front face 7, a back face 9, a top face 6, a bottom face 8, and side faces 10a and 10b. Within the array 3, the articles 5 are placed with at least a portion of their front faces 7 in a contacting relationship. Similarly, at least of a portion of the back faces 9 of the articles 5 are in a contacting relationship. Each article 5 includes an upper section 11 and a lower section 13.

Referring again to FIG. 1 and FIG. 2, all the upper sections 11 are located in the first region 15 of the array 3 of articles 5. As the first region 15 of the array 3 of the articles 5 has a larger size, or a higher compression resistance when considering compressed packaging, than the second region 17, the first region 15 of the array 3 of the articles 5 will have a larger size or volume than the second region 17. In compressed packaging, the first region 15 of the array 3 of the articles 5, especially when the articles 5 are absorbent articles, have a larger size or volume after compression than the second region 17. A package 1 of irregular or non-uniform dimensions is the result, e.g., such as non-rectangular or non-square. Under such situations, the second region 17 of the package 1 will not be filled. For example, when a rectangular shaped outer casing 19 is used for the package 1, the second region 17 of the package 1 will not be filled.

Figure 6:
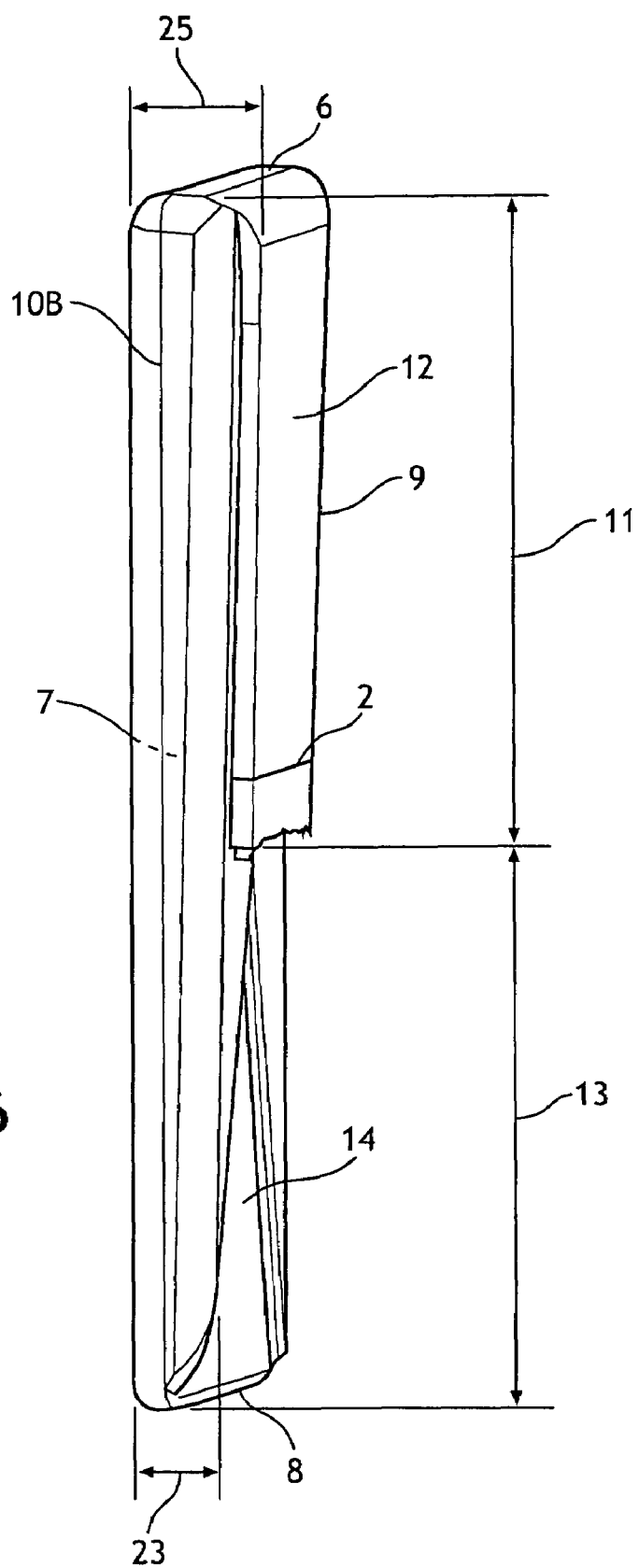
FIG. 6 shows a perspective view of a packaging article side view in folded condition.

Referring now to FIG. 5 and FIG. 6, an embodiment of a folded article 5 is shown wherein the lower section 13 includes a gap 23 such that the size of the lower section 13 is decreased in comparison to the size of the upper section 11. However, the present invention operates with non-absorbent articles as well. Alternatively, if compressed packaging is utilized, the embodiment of the folded article 5 and the lower section 13 includes a gap 23 such that the compressibility of the lower section 13 is increased in comparison to the compressibility of the upper section 11. For many bi-folded articles 5, especially absorbent articles, the configuration of FIG. 5 will result as the caliper 23 corresponding to the crotch regions 14 of an article 5 is less than the caliper 25 corresponding to the waist regions 12 of the articles 5. In the folded article 5 of FIG. 6, the crotch region 14 forms the bottom section 13, and the waist regions 12 form the top section 11. Identifying number 2 marks the back of the folded product with a colored thread.

Figure 7:
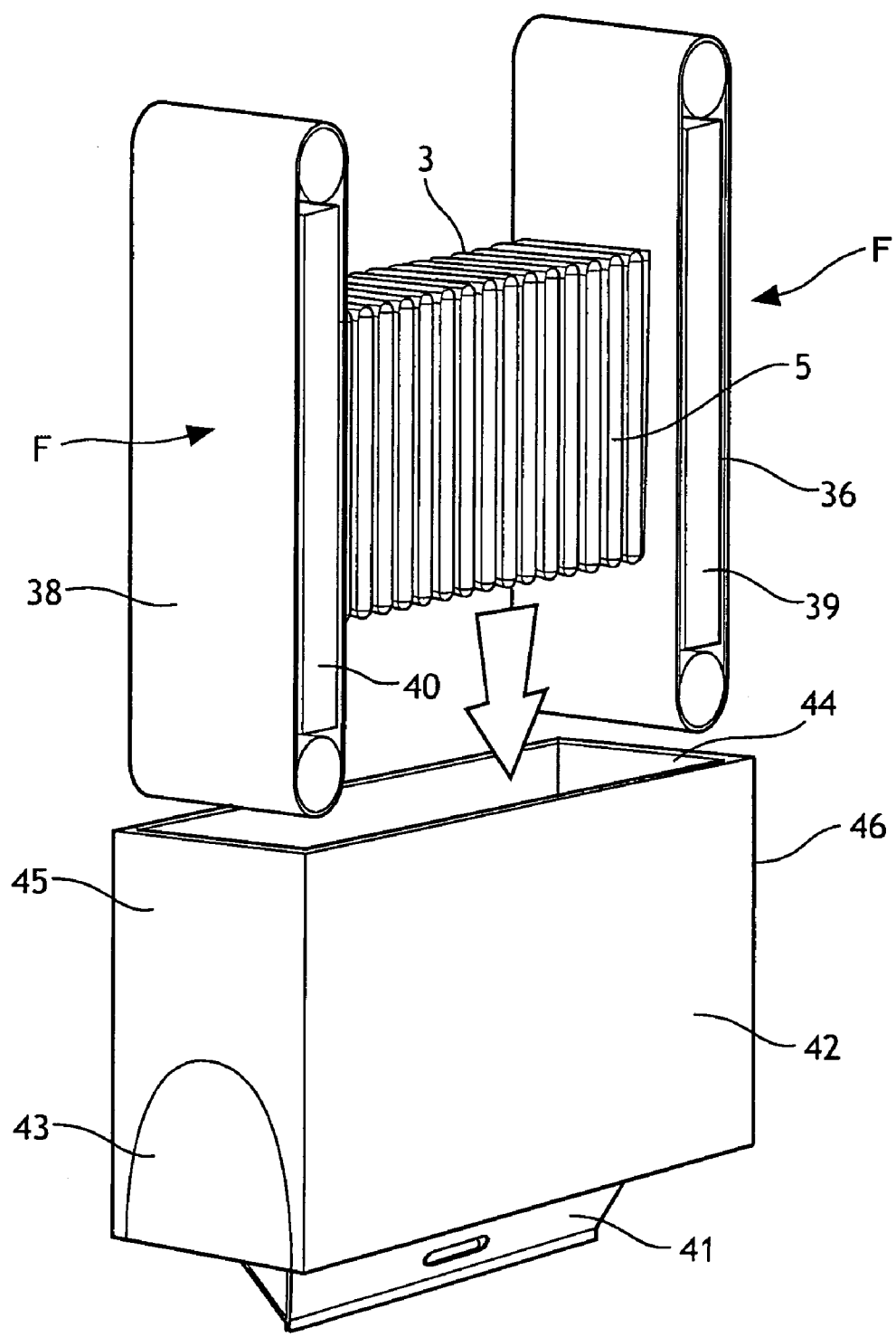
FIG. 7 shows a perspective view of a compression packaging apparatus.

Referring now to FIG. 7, a schematic view of array 3 of articles 5 is aligned between two belts 36 and 38. Where compressed packaging is used, compression is applied to individual articles 5, articles 5 in an array 3, or to both the individual article 5 and the array 3. Where compression is applied to articles in an array, the belts 36 and 38 are compression belts. Each belt 36 and 38 includes a member 39 and 40, respectively. Each belt 36 and 38 provide compression force to the array 3 of the articles 5. When compression force is applied, the array 3 of the articles 5 is compressed to between about 0% and 90% of its uncompressed volume, preferably about 0% and about 80%, more preferably about 10% and 75%, most preferably about 20% and about 70% of its uncompressed volume in the direction of the arrows F by moving the members 39 and 40 together with a force as great as 2000 kg.

After alignment or compression of the array 3, the belts 36 and 38 are inserted through a bottom surface 44 of a bag 42, as shown in FIG. 7. The array 3 of articles 5 is inserted into the bag 42 by rotation of the belts 36 and 38. After the array 3 has been inserted into the bag 42, the belts 36 and 38 are retracted from the bag 42, which is sealed subsequently on the bottom surface 44. Loading of the array 3 of the articles 5 also is accomplished by using a pusher system. The bag 42 includes a handle 41 and an opening device 43, formed by a line of weaknesses or perforations on one of the side surfaces 45 or 46 of the bag 42. Accordingly, one method of packaging compressed articles 5 is provided. The present invention is not intended to be limited to one particular embodiment for packaging compressed articles 5.

Figure 8:
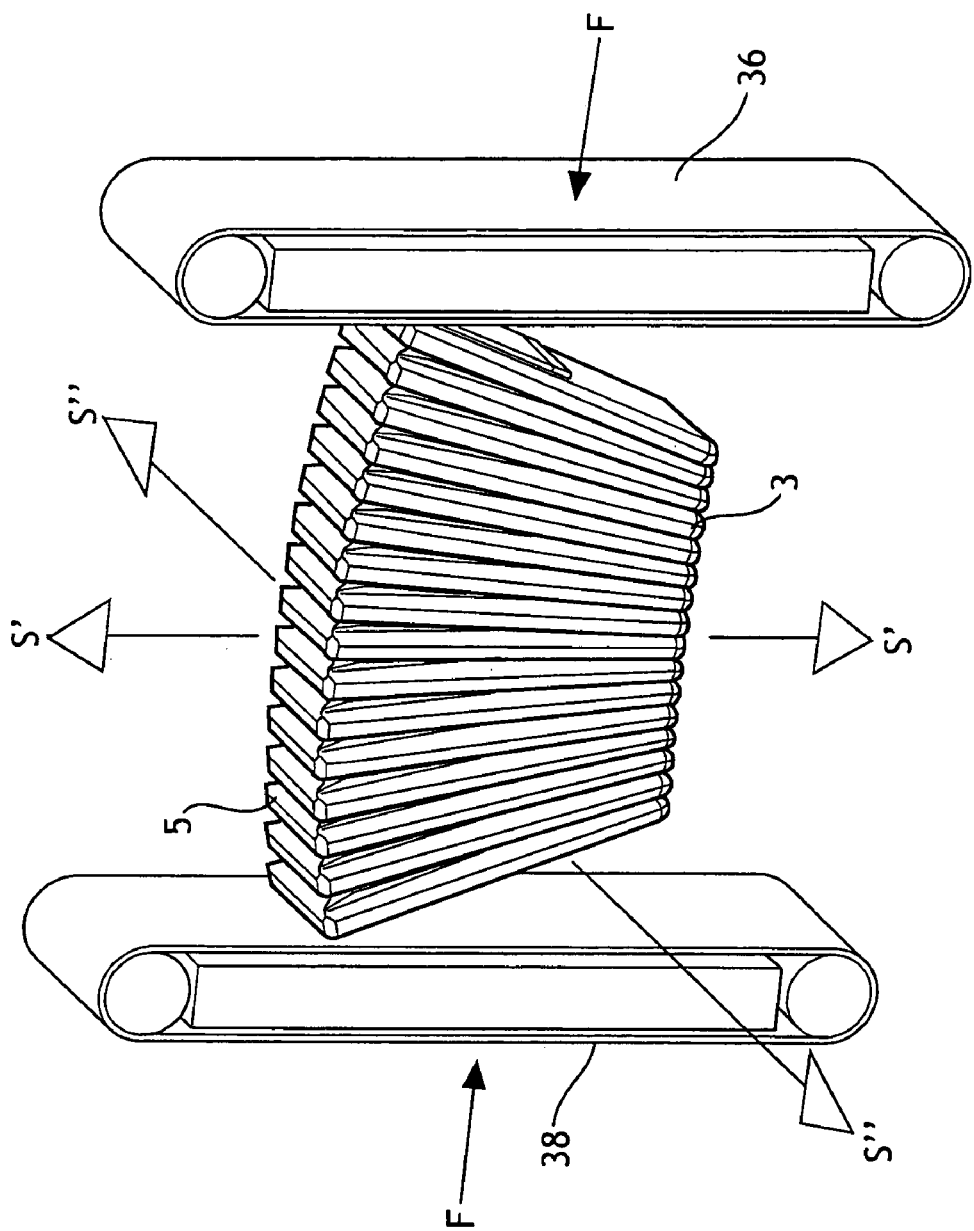
FIG. 8 shows a perspective view of a compression packaging apparatus with a uniformly stacked packaging article package.

Referring now to FIG. 8, in compression of the array 3 of the articles 5 between the compression belts 36 and 38, each article 5, absorbent or otherwise, is squeezed tightly in the first region 15 of the array 3. The squeezing causes the articles 5 to be squeezed out of the array 3 in the direction of the arrows S or S', S" or S'" depending on the uniformity of the articles 5. Because of the movement of the articles 5 within the array 3, additional compression restraining means operate to prevent a break up of the array 3.

Figure 9:
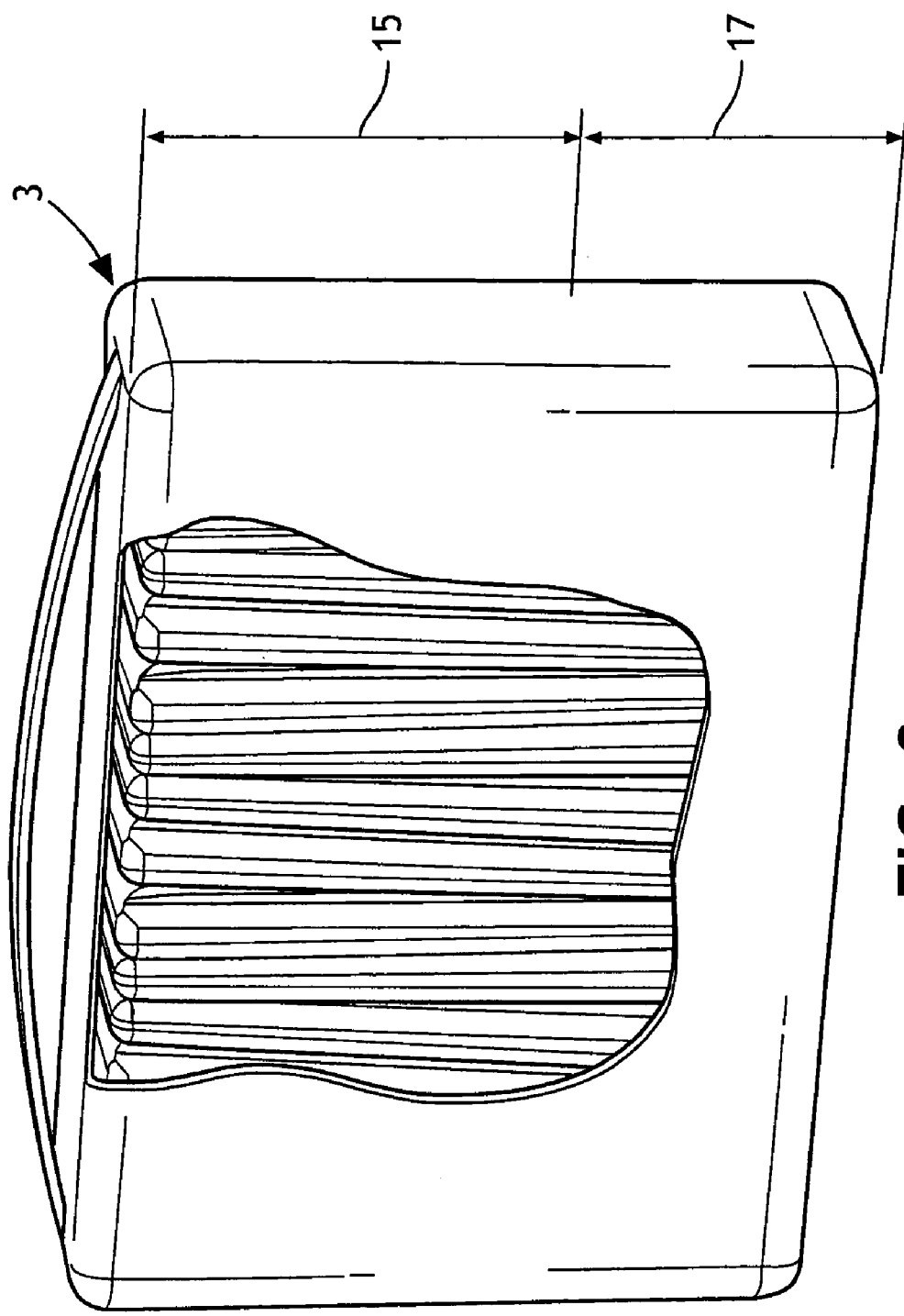
FIG. 9 shows a cut away view of an array of articles, such as absorbent articles, in a stacked product.
Figure 10:
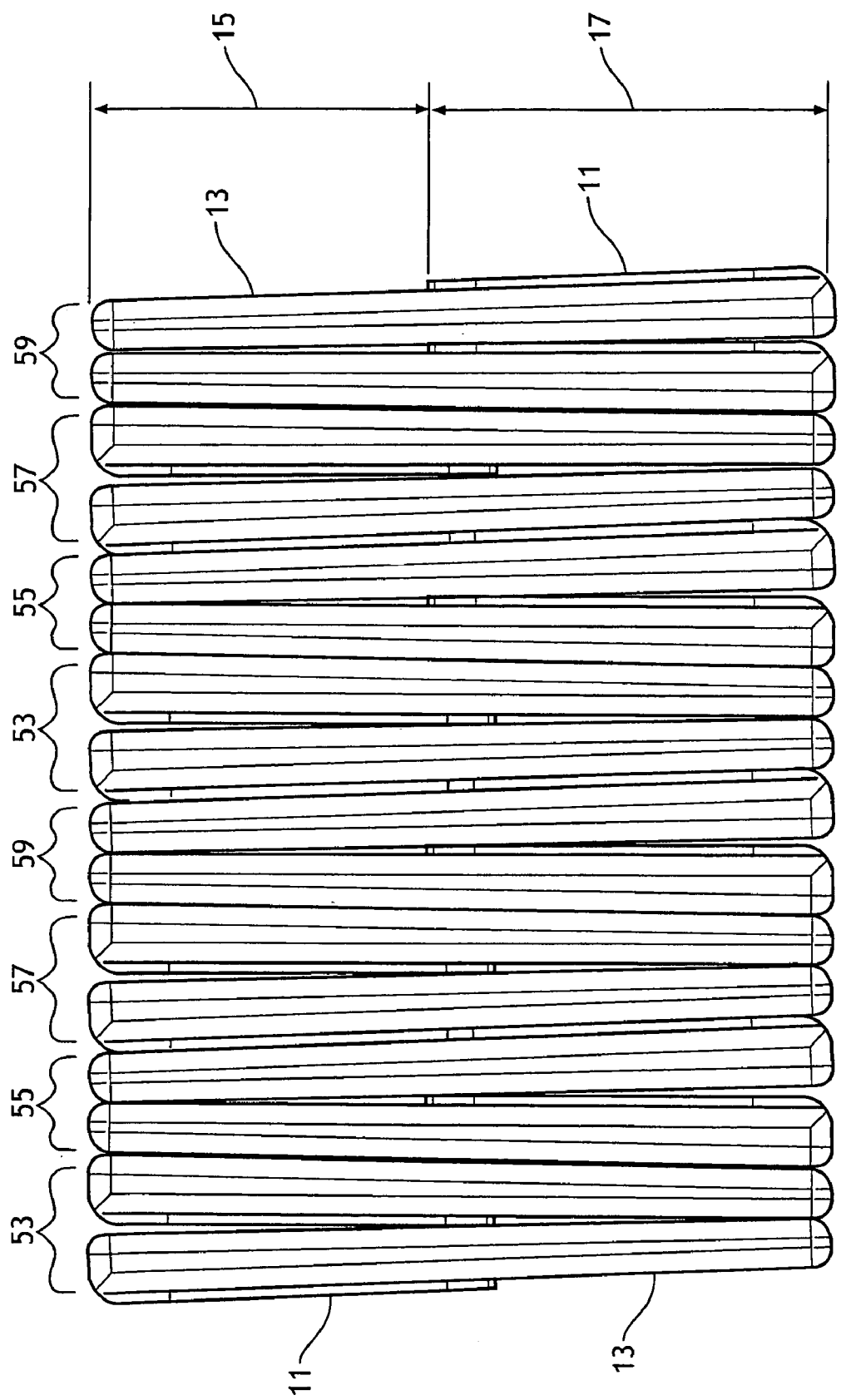
FIG. 10 shows a side view of an array of articles, such as absorbent articles, in a stacked product.
Figure 11:
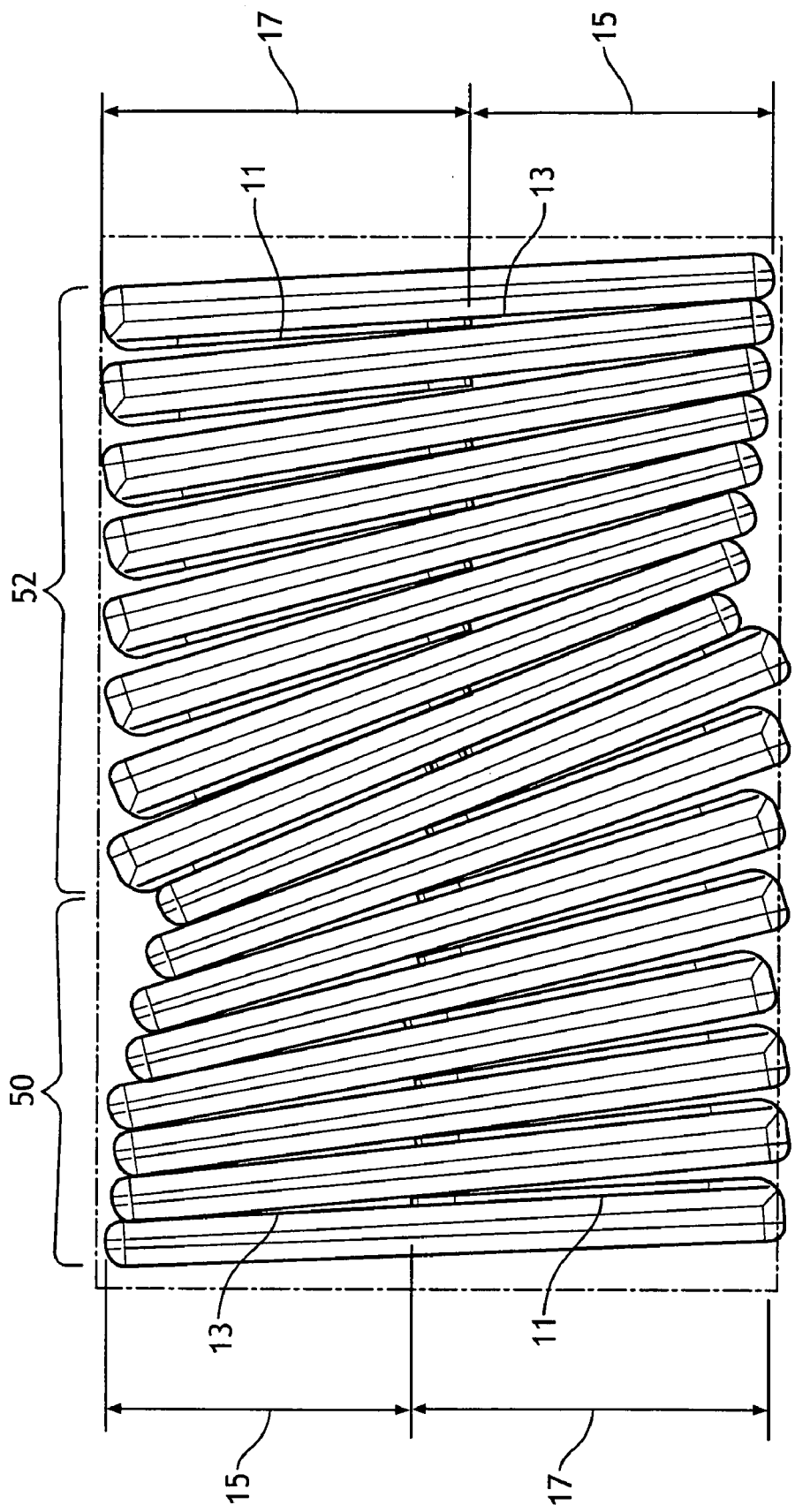
FIG. 11 shows a side view of an array of articles, such as absorbent articles, having an alternatively stacked product.

Referring now to FIG. 9 and FIG. 10, the articles 5, absorbent or otherwise, are arranged into groups 53, 55, 57, and 59 such that the upper sections 11 of the articles 5 in groups 53 and 57 are located in the first region 15 of the array 3 of the articles 5, and the upper sections 11 of the articles 5 in groups 55 and 59 are located in the second region 17 of the array 3 of the articles 5. The number of the articles 5 contained in each group varies from 2, as illustrated in FIG. 11 to half the number of the articles 5 in the package 1, as illustrated in FIG. 1. The preferred embodiment occurs when the number of groups are equal to each other, each group comprising a predetermined equal number of the articles 5.

Referring now to FIG. 3, a different configuration of the articles 5 is shown within the array 3. As shown in FIG. 3, the predetermined number of the articles 5 in the common orientation of the front face 7 to back face 9 contacting relationship of the articles 5 is changed to a front face 7 to front face 7 or back face 9 to back face 9 contacting relationship of the present invention for the same predetermined number of the articles 5 wherein the bottom face 8 to bottom face 8 or top face 6 to top face 6 contacting relationship of the common orientation is changed to a bottom face 8 to top face 6 contacting relationship of the present invention.

Figure 12:
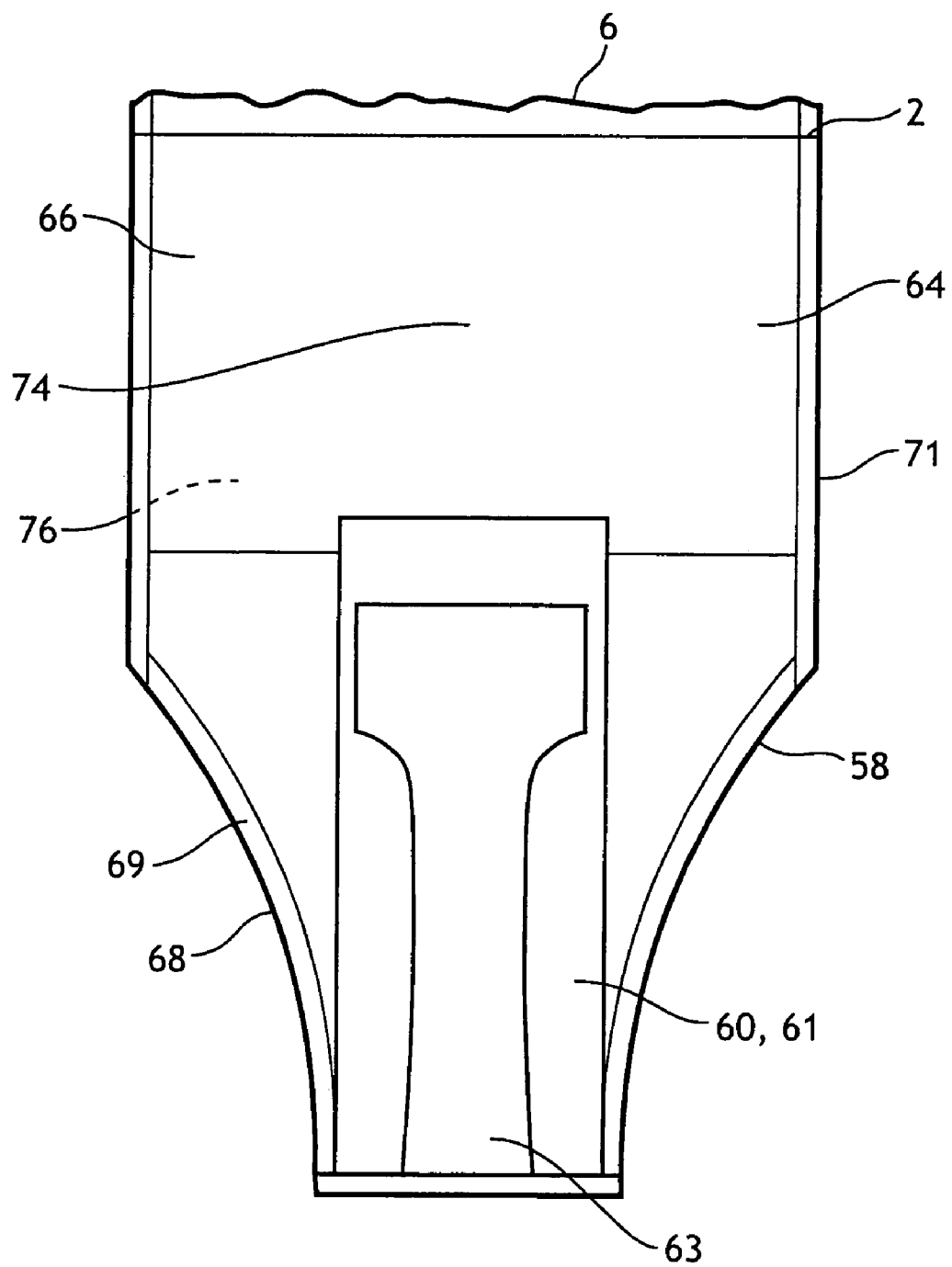
FIG. 12 shows a back view of an absorbent article.

Referring now to FIG. 12, a plan view is shown of a flattened disposable article 58, such as a pant. The article 58 includes a liquid pervious topsheet 60 and a liquid impervious backsheet 61.

In FIG. 12, the article 58 includes an absorbent core 63, including cellulosic fibers and hydrogel forming particles. The absorbent core 63 includes a structure or material used for the absorption of bodily fluids, without intending to limit the absorbent core 63 to the structure described. Leg elastic elements 69 are located in the leg regions 68 of the article 58. Front and back fit elastics 66 in the corresponding front and back regions 76 and 74 are provided in the article 58. A fastening system 71 alternatively includes mechanical fasteners or a combination of adhesive fasteners and mechanical fasteners.

Figure 13:
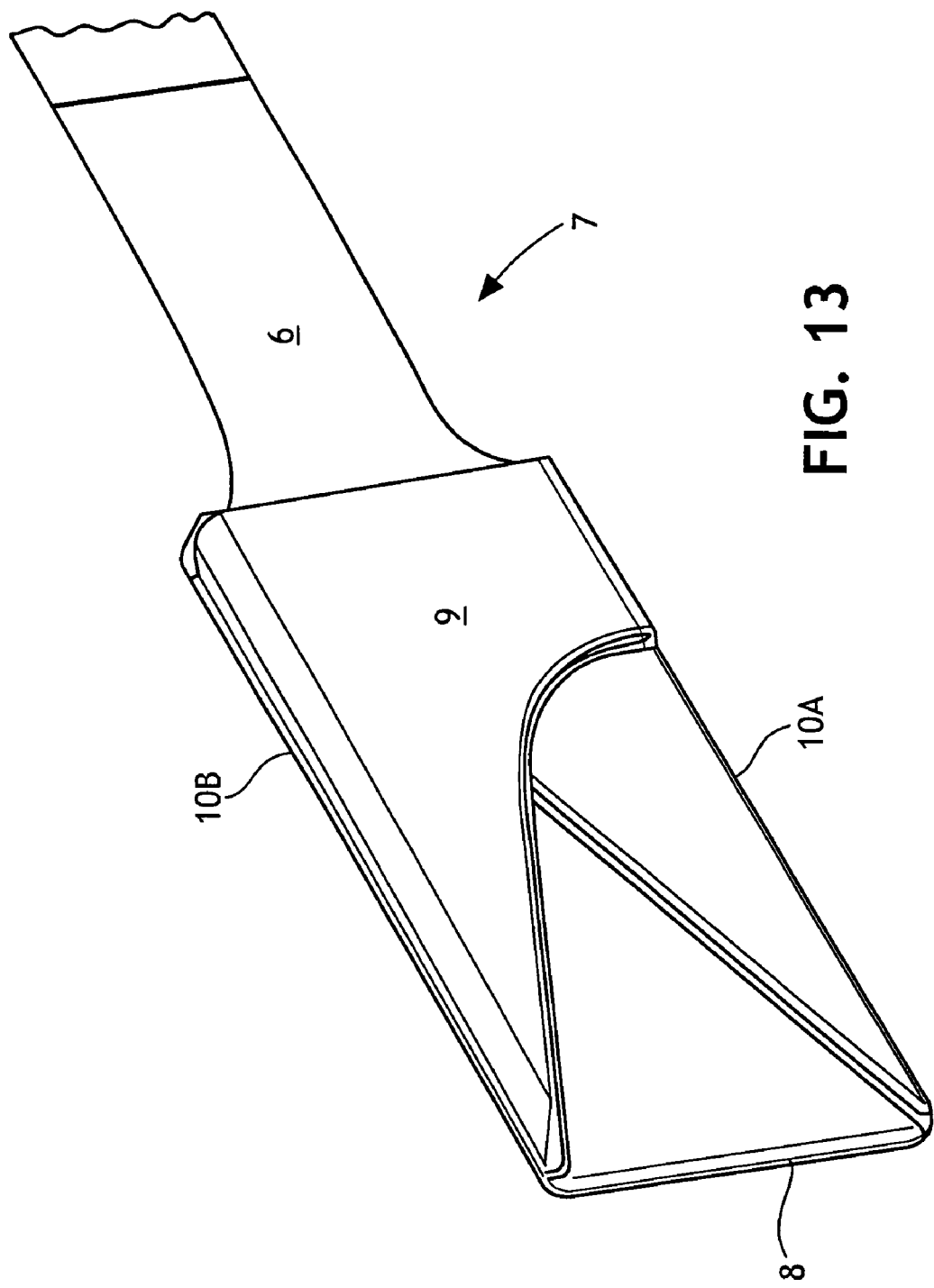
FIG. 13 shows a perspective view of a disposable diaper in partially folded flattened state.

In FIG. 13, each partially folded article 5 includes a front face 7 (not shown), a back face 9, a top face 6, a bottom face 8, and a pair of side faces 10A and 10B. Within the array 3, the articles 5 are placed with at least a portion of their front faces 7 in a contacting relationship. Similarly, at least a portion of the back faces 9 of the articles 5 are in a contacting relationship. Each article 5 includes an upper section 11 and a lower section 13.

The packaging article and method of the present invention position a product so that a front of adjacent products contacts a front, and a back of adjacent products always contacts a back of a product.

The packaging article and method of the present invention include a packaged array of flexible articles housed in a flexible outer casing. In one embodiment, an array of absorbent articles has a first region and a second region. Each article provides a top face, a bottom face, a front face, a back face, and a pair of side faces distributed over the first and second region of the array of articles. An upper section and a lower section have mutually different calipers, wherein by caliper is meant thickness or bulk.

Conversely to a packaging process wherein absorbent articles are aligned in an array having a back face of one article in contacting relationship with a front face of an adjacent article, and a bottom face of a first article adjacent a bottom face of an adjacent article, according to the configuration of articles within the array of present invention, at least a portion or a predetermined number of articles within the array are in a front face to front face contacting relationship with adjacent articles or, alternatively, in a back face to back face contacting relationship. At least a portion or a predetermined number of articles within the array are in a top face to bottom face relationship with adjacent articles. The articles in a front face to front face contacting relationship with adjacent articles or alternatively in a back face to back face contacting relationship are the articles in the top face to bottom face relationship with the adjacent articles.

Conventional package arrays of compressed articles surrounded by a covering made from a film of thermoplastic material such that each unit package are maintained in a compressed condition by a paper wrapping or container.

The packaging article and method of the present invention have novelty over conventional means and methods of packaging in one aspect by not requiring or using a compressing covering material such as a compressing paper wrap.

The packaging article and method of the present invention position the product so that the compressed condition is not required because of the method of packaging not involving a carton.

The packaging article and method of the present invention provide an important difference in the sizes or the compression forces for compression of absorbent articles, for compressed packaging of the first and second regions when the upper and lower sections are distributed throughout the array of articles. The difference is at least 10% when compared to the differences in the sizes of the articles or the compression forces for compression of the articles when compressed packaging is utilized for the largest region when all the upper sections of the articles are located in the same region of the array of the articles. When a compression force is applied to the articles, the articles are compressed to between about 10% to about 75% of an uncompressed volume.

By redistributing the orientation or configuration of the articles within the array before packaging, the packaging of the array of the articles becomes uniform. When compressed packaging is utilized, the array of articles is reoriented before compression force is applied to the array. The array of articles is more stable for processing when reoriented in accordance with the present invention prior to the compression. The difference in the size of the upper and lower sections of the articles in the reoriented array is reduced to obtain an equal distribution of the articles or volume of the first and second regions.

Reorientation in accordance with the present invention provides for use of volume or space within the outer casing. Reorientation in accordance with the present invention prevents over-compression of various parts of the articles where compressed packaging is utilized. Reorientation in accordance with the present invention reduces or prevents damage to absorbent articles and a tendency for the articles to pop out of the outer casing during handling is reduced.

Using the reoriented configuration of the present invention for the array of articles, more articles are included in a single array before the array becomes unstable. In this way, the packaging process is simplified, and the speed of the production of the articles is increased while providing a more stable product package having the advantages of the present invention.

Load bearing properties and shape stability of the packaging article and method of the present invention are increased. The reoriented array of absorbent articles and method of the present invention is stacked in a more stable manner for shipping, handling, and display.

It has been found that a package according to the present invention can be compressed by at least 10% more in the direction of compression in comparison to a package of an equal number of articles wherein all the upper sections are located in the same region of the array of the articles.

In one embodiment of packaging according to the present invention, the articles are distributed within the array such that the sizes or the compression forces for the first and second regions of the array of the articles are equal. In this way, the packaging apparatus accommodates the need for a variety of bag sizes. When compressed packaging is used, the compression apparatus is simplified as the pivoting preventive support for the compression plates to accommodate the different compressibilities of the array of articles is reduced.

The array of the absorbent articles is oriented in such a manner that after compression the expansion force of the first region of the array is equal to the expansion force of the second region to counteract deformation of the package during removal of the compression forces.

An array of articles in accordance with the present invention is formed by stacking bi-folded absorbent articles, e.g., diapers, together having either non-uniform caliper or have low and high density regions. In one aspect, a bi-folded diaper is folded once on itself at its crotch region. Bi-folded diapers have a rounded upper section and a high compression resistance corresponding to the crotch region of the unfolded diaper and a lower section with a low compression resistance corresponding to the waist regions of the unfolded diaper. The preferred packaging advantage feature of the packaging of the present invention is provided when the orientation of the rounded upper sections is alternated within the array of the absorbent articles. The orientation of the upper sections is alternated for groups of two or more articles, and the number of rounded upper sections in the first and second regions of the array of compressed diapers is not equal. In one aspect, absorbent articles are tri-folded or bi-tri-folded.

Compressibility reduces volume when a predetermined force is applied to an article or to an array of absorbent articles. Reduction in volume of the packaging article and method of the present invention is between 20% and 70% of the uncompressed volume.

It has been found empirically that the packaging article and method of the present invention provides key differences in respect to the compressibility, volume, and structure of the package produced.

It has been found that the packaging article and method of the present invention resolve issues encountered when packaging a taper shaped folded product. It has been found empirically that the present invention as developed provides more than just uniform stacks. It has been found that the present invention as developed provides process friendly and efficient packaging operations. The present invention provides an ability to obtain greater compression ratios and an ability to store more products in less space reducing shipping cost. The invention provides an ability to run packaging operations of tapered shaped folded products with fewer disruptions to operations. The invention provides an ability to re-enter product into the packaging that was wasted before. The invention provides for reducing packaging costs of taper-shaped folded products to save millions of dollars per year. The difference is important in today's highly competitive market.

The present invention positions the product so that the compressed condition is not required because of the method of packaging not involving a carton.

The present invention is completely different in the means and method of packaging not requiring or using a compressing covering material such as a compressing paper wrap.

The present invention positions the product so that the compressed condition is not required because of the method of packaging not involving a carton.

The present invention provides an array of articles formed by stacking bi-folded absorbent articles, e.g., diapers, together having either non-uniform caliper or have low and high density regions. In one respect, a bi-folded diaper is folded once on itself at its crotch region. Bi-folded diapers have a rounded upper section and a high compression resistance corresponding to the crotch region of the unfolded diaper and a lower section with a low compression resistance corresponding to the waist regions of the unfolded diaper. The packaging advantage of the present invention is provided when the orientation of the rounded upper sections is alternated within the array of the absorbent articles. The orientation of the upper sections is alternated for groups of two or more articles, and the number of rounded upper sections in the first and second regions of the array of compressed diapers is not equal. In one aspect, absorbent articles are tri-folded or bi-tri-folded.

The package articles and methods of the present invention are not intended to be limited to the specific embodiments described in the description of the specification and shown in the figures of the drawings and are intended to cover all embodiments included in the claims of the patent which follow.

Conventional packaging, e.g., such as for disposable diapers, positions the packaged article product in an array so that the front and back sides of the articles are in contact in the array in the package.

The package and method of the present invention, on the other hand, positions the articles, e.g., such as for disposable diapers, of the packaged article product so that the front of adjacent article products contacts the front of the adjacent article, and the back of adjacent article products contacts the back of the adjacent product article in the array of the package.

Conventional package arrays of compressed articles are required to be surrounded by a covering made from a film of thermoplastic material such that each unit package is maintained in a compressed condition by a paper wrapping.

The package and method of the present invention provide means and method of packaging not requiring or using a compressing covering material such as a paper wrap as used in conventional packaging.

Rather, the package and method of the present invention position the product so that the compressed condition is not required because of the method of packaging not involving a carton.

The package and method of the present invention provide an important difference in the size or the compression force for compression of absorbent articles. The compressed packaging of the first and second array regions, when the upper and lower article sections are distributed throughout the array of articles, is at least 10% smaller than the difference in the size of the articles or the compression force for compression of the articles when compressed packaging is being utilized for compression of the largest array region when all the upper article sections of the articles are located in the same array region of the array of the articles. When a compression force is applied to the articles, the articles are compressed to between about 10% to about 75% of an uncompressed volume.

It has been found that by redistributing the orientation or configuration of the articles within the array before packaging in the package and method of the present invention, the packaging of the array of the articles becomes more uniform. When compressed packaging is utilized, the array of articles in the package and method of the present invention is reoriented before the compression force is applied. It has been found that the array of articles is more stable for processing if reoriented prior to the compression. The difference in the size of the upper and lower sections of the articles in the reoriented array is reduced to obtain an equal distribution of the articles or volume of the first and second regions.

The compressibility reduction in volume, from a predetermined force is applied to an article or to an array of absorbent articles, has been found empirically that for the package and method of the present invention that key differences in respect to the compressibility, volume, and structure of the package are produced. Reduction in volume is at least 10% and preferably between 20% and 70% of the uncompressed volume.

Conventional package arrays of absorbent articles are placed with the front and back faces in a contacting relationship. The package and method of the present invention require an orientation completely different from conventional packaging in orientation. Conventional packaging positions the product so that the front and back sides are always in contact. The package and method of the present invention position the product so that the front of adjacent products articles contacts the front, and the back of adjacent products articles always contacts the back of the product articles whenever product articles are in contact in the array of the product articles. The package and method of the present invention use a horizontal stacker instead of a vertical stacker, which is unique and provides an packaging process sewing as an alternative method of stacking product.

The package and method of the present invention solve problems because of issues encountered when packaging a taper-shaped folded product. It has been found empirically that the package and method of the present invention provide more than just uniform stacks. The package and method of the present invention have been found to provide process friendly and efficient packaging operations. The package and method of the present invention have been found to provide an ability to obtain greater compression ratios and to store more products in less space, reducing shipping cost. The package and method of the present invention provide an ability to run packaging of taper-shaped folded products with fewer disruptions to operations. The package and method of the present invention provide an ability to re-enter product into the packaging that was wasted before. The package and method of the present invention provide for reducing packaging cost of taper-shaped folded products thereby to save millions of dollars per year. The difference is important in today's highly competitive market for packaged disposable absorbent articles.

Conventional packaged arrays of compressed articles are surrounded by a covering made from a film of paper or thermoplastic material such that each unit package is maintained in a compressed condition by a paper or thermoplastic wrapping.

The package and method of the present invention provide the means and method of packaging not requiring or using a compressing covering material such as a paper or thermoplastic wrap as used in conventional packaging of arrays. The package and method of the present invention rather position the product so that the compressed condition is not required because of the method of packaging not involving a carton.

Conventional packaging has not used arrays configured in an array including the front and back faces being in contacting relationship as configured in the package and method of the present invention requiring front faces in contact and back faces in contact.

The package and method of the present invention provide an important difference in the size or the compression force for compression of absorbent articles. For compressed packaging of the first and second array regions when the upper and lower article sections are distributed throughout the array of articles, size or the compression force required for the package and method of the present invention is at least 10% smaller than the difference in the size of the articles or the compression force for compression of the articles when compressed packaging is being utilized of the largest region when all the upper article sections of the articles are located in the same array region of the array of the articles. When a compression force is applied to the articles, the articles are compressed to between about 10% to about 75% of an uncompressed volume.

By redistributing the orientation or configuration of the articles within the array before packaging, the packaging of the array of the articles becomes more uniform. When compressed packaging is utilized, the array of articles is reoriented before the compression force is applied. The array of articles is more stable for processing if reoriented prior to the compression. The difference in the size of the upper and lower article sections of the articles in the reoriented array is reduced to obtain an equal distribution of the articles or volume of the first and second array regions.

Reorientation provides for use of volume or space within the outer casing. Reorientation prevents over-compression of various parts of the articles where compressed packaging is utilized. Reorientation reduces or prevents damage to absorbent articles and has been found to eliminate a tendency for the articles to pop out of the outer casing during handling.

Using the reoriented configuration of the present invention for the array of articles, more articles are included in a single array before the array becomes unstable. In this way, the packaging process is simplified, and the speed of the production of the articles is increased while providing a more stable product package having the advantages of the present invention.

Load bearing properties and shape stability of the package are increased. The reoriented array of absorbent articles is stacked in a more stable manner for shipping, handling, and display.

It has been found that a package and method according to the present invention can provide a package compressed by a factor at least 10% more in the direction of compression in comparison to a package of an equal number of articles wherein all the upper sections are located in the same region of the array of the articles.

In one embodiment of packaging according to the present invention, the articles are distributed within the array such that the size or the compression force for the first and second array regions of the array of the articles are equal. In this way, the packaging apparatus accommodates the need for a variety of bag sizes. When compressed packaging is used, the compression apparatus is simplified as the pivoting preventive support for the compression plates to accommodate the different compressibilities of the array of articles is reduced.

The array of the absorbent articles is oriented in such a manner that after compression the expansion force of the first region of the array is equal to the expansion force of the second region to counteract deformation of the package during removal of the compression forces.

An array of articles is formed by stacking bi-folded absorbent articles, e.g., diapers, together having either non-uniform caliper or have low and high density regions. In one respect, a bi-folded diaper is folded once on itself at its crotch region. Bi-folded diapers have a rounded upper section and a high compression resistance corresponding to the crotch region of the unfolded diaper and a lower section with a low compression resistance corresponding to the waist regions of the unfolded diaper. The packaging advantage of the present invention is provided when the orientation of the rounded upper sections is alternated within the array of the absorbent articles. The orientation of the upper sections is alternated for groups of two or more articles, and the number of rounded upper sections in the first and second regions of the array of compressed diapers is not equal. In one aspect, absorbent articles are tri-folded or bi-tri-folded.

Compressibility reduces the volume when the predetermined force is applied to the article, flexible article, or to the array of absorbent articles. Reduction in volume is at least 10% and preferably 15%, more preferably between 20% and 70% of the uncompressed volume. Conventional package arrays of compressed articles are surrounded by a covering made from a film of thermoplastic material such that each unit package is maintained in a compressed condition, e.g., such as by a paper wrapping. The package and method of the present invention provide the means and method of packaging not requiring or using a compressing covering material such as a paper or thermoplastic wrap as used in conventional packaging.

It has been found empirically the package and method of the present invention provide key differences in respect to the compressibility, volume, and structure of the package produced. The package and method of the present invention require an orientation completely different from conventional packaging in orientation. Conventional packaging positions the product so that the front and back sides are always in contact. The package and method of the present invention position the product so that the front of adjacent products contacts the front, and the back of adjacent products always contacts the back of the product.

The package and method of the present invention preferably can use a horizontal stacker instead of a vertical stacker, thereby providing a preferable alternative method of stacking product.

The package and method of the present invention provide a solution to issues encountered in packaging a taper-shaped folded product. It has been found empirically that the package and method of the present invention as developed provides more than uniform stacks. It has been found to that the package and method of the present invention provide more efficient processing more and efficient packaging operations. The invention has been found to provide an ability to obtain greater compression ratios and to store more products in less space, thereby reducing shipping cost. The invention has been found to provide an ability to run packaging of tapered shaped folded products with fewer disruptions to operations. The invention has been found to provide an ability to re-enter product into the packaging that was wasted before. The invention provides for reducing packaging cost of taper shaped folded products to save millions of dollars per year. These differences are important in today's highly competitive market for packaging and distribution of disposable flexible or diapers.

The package in accordance with the present invention contains an array of flexible articles, each article having an article front face, an article back face, an article top face, an article bottom face, article side faces, an upper article section and a lower article section, the article sections having mutually different caliper; wherein each article in contact with another article is placed with an article front face in contact with an article front face or wherein each article in contact with another article is placed with an article back face in contact with an article back face; the array having a first array region and a second array region, the upper and lower article sections being distributed over the first and second array regions of the array, wherein the upper and lower article sections are distributed such that a reordered size difference of the first and second array regions is at least about 10% smaller than when all of the upper article sections are located in the same array region of the array.

The mutually different caliper of the article sections consists of a caliper in the upper article section different from the lower article section. The package contains no compressing paper wrapping required to maintain the array of the article. The upper and lower article sections of each articles are distributed such that the sizes of the first and second array regions of the array are substantially equal. Each article in contact with another article is placed with the article bottom faces in a contact with the top faces of adjacent articles. The reordered size difference is at least about 15% smaller. The dimension of the first array region of the array is substantially equal to the dimension of the second array region of the array. The mutually different caliper of the article sections consists of a caliper in the upper article section different from the lower article section.

The package in accordance with the present invention includes a flexible outer casing containing an array of compressed, flexible absorbent articles, each article including an article front face, an article back face, an article top face, an article bottom face, article side faces, an upper article section and a lower article section, the article sections having mutually different compressibilities and calipers; wherein at least a portion of the absorbent articles are placed with the article front faces in a contacting relationship and at least a portion of the absorbent articles are placed with the article back faces in a contacting relationship; the array having a first array region and a second array region and the upper and lower article sections of each articles being distributed over the first and second array regions of the array; wherein the distribution of the upper and lower article sections is such that the difference in the compression force for compression of the first and second array regions to between 0% and 90% of an uncompressed volume is at least 10% smaller than the difference in the compression force for compression of the first and second array regions when all of the upper article sections of each articles are located in the same array region of the array; and the flexible outer casing maintains the array of compressed articles.

The upper and lower article sections are distributed in such a way that the compression forces for the first and second array regions of the array are substantially equal. The article bottom faces in a contacting relationship form a reoccurring stack pattern with the article top faces of adjacent articles. The orientation of each articles is periodically alternated. After compression, the dimension along the direction of compression of the first array region of the array is equal to the dimension along the direction of compression of the second array region of the array. After compression, the expansion force of the first array region is equal to the expansion force of the second array region. The absorbent articles consist of different caliper in the upper and lower article sections. The absorbent articles consist of different caliper in the upper and lower article sections.

The package in accordance with the present invention includes an array of disposable diapers, the disposable diapers including a diaper front face, a diaper back face, a diaper top face, a diaper bottom face, diaper side faces, an upper diaper section and a lower diaper section, the diaper sections having mutually different calipers, wherein at least a portion of the disposable diapers are placed with the diaper front faces in a contacting relationship and at least a portion of the diaper back faces in a contacting relationship; further including a flexible outer casing; the array having a first array region and a second array region and the upper and lower diaper sections of the disposable diapers being distributed over the first and second array regions of the array, wherein the distribution of upper and lower diaper sections is such that the difference in size of the first and second array regions is at least about 10% smaller than when all of the upper diaper sections of the absorbent disposable diapers are located in the same array region of the array.

The upper and lower diaper sections of the disposable diapers are distributed such that the sizes of the first and second array regions of the array are substantially equal. At least a portion of the disposable diapers are placed with the diaper bottom faces in a contacting relationship forming a reoccurring stack pattern with the top faces of adjacent disposable diapers. The orientation of the disposable diapers is periodically alternated. The dimensions of the first array region of the array are equal to the dimensions of the second array region of the array. The disposable diapers consist of different calipers in the upper and lower diaper sections. The package does not contain compressing wrapping required to maintain the array of the disposable diapers.

The package in accordance with the present invention contains an array of compressed, flexible disposable diapers, the disposable diapers including a diaper front face, a diaper back face, a diaper top face, a diaper bottom face, diaper side faces, an upper diaper section and a lower diaper section, the diaper sections having mutually different compressibilities and calipers; wherein at least a portion of the disposable diapers are placed with the disposable front faces in contacting relationship and at least a portion of the diaper back faces in contacting relationship; further including a flexible outer casing; the array having a first array region and a second array region and the upper and lower diaper sections of the disposable diapers being distributed over the first and second array regions of the array, wherein the distribution of the upper and lower diaper sections is such that the difference in the compression force for compression of the first and second array regions to between 0% and 90% of an uncompressed volume is at least 10% smaller than the force for compression of the first and second array regions when all of the upper diaper sections of the disposable diapers are located in the same array region of the array; and the flexible outer casing maintains the array of the compressed disposable diapers.

The upper and lower diaper sections of the disposable diapers are distributed in such a way that the compression forces for the first and second array regions of the array are substantially equal. At least a portion of the disposable diapers are placed with the diaper bottom faces in contacting relationship forming a reoccurring stack pattern with the top faces of adjacent disposable diapers. The orientation of the disposable diapers is periodically alternated. The dimension along the direction of compression of the first array region of the array is equal to the dimension along the direction of compression of the second array region of the array. After compression, the expansion force of the first array region is equal to the expansion force of the second array region. The disposable diapers consist of different calipers in the upper and lower diaper sections. The package does not require compressing wrapping to maintain the array of the compressed disposable diapers.

The method in accordance with the present invention forms a package, including transporting a plurality of articles in a consecutive manner to a folding unit, folding each article, changing the orientation of each article at regularly spaced intervals, aligning a predetermined number of each article with an article front face or an article back face in a contacting relationship such that the article front face contacts another front face or an article back face contacts an article back face of an adjacent article to form an uncompressed array. A predetermined number of each articles have an upper article section located in a first array region of the array and a second predetermined number of each articles have an upper article sections located in a second array region of the array. The method includes placing the array in a flexible outer casing.

The method in accordance with the present invention forms a package, including the following steps of transporting a plurality of flexible, absorbent articles in a consecutive manner to a folding unit; folding each flexible, absorbent article; changing the orientation of each flexible, absorbent article at regularly spaced intervals; aligning a predetermined number of each flexible, absorbent articles in adjacent contact to have an article front face in contact with an article front face or an article back face in contact with an article back face to form an uncompressed array, wherein a predetermined number of each flexible, absorbent articles have an the upper article section located in a first array region of the array; compressing the array; and placing the compressed array in a flexible outer casing.

A second predetermined number of each flexible, absorbent article have an upper article section located in a second array region of the array.

The method in accordance with the present invention forms a package, including transporting disposable diapers in a consecutive manner to a folding unit; folding each disposable diaper; changing the orientation of the disposable diapers at regularly spaced intervals; aligning a predetermined number of the disposable diapers with a diaper front face or a diaper back face in a contacting relationship such that front faces contact front faces or back faces contact back faces to form an uncompressed array, wherein a predetermined number of the disposable diapers have an upper diaper section located in a first array region of the array and a second predetermined number of the articles have an upper article section located in a second array region of the array; compressing the array; and placing the compressed array in a flexible outer casing.

The compression force is substantially uniform across the first and second array regions.

The method in accordance with the present invention forms a package, including the following steps of transporting disposable diapers in a consecutive manner to a folding unit; folding the disposable diapers; and changing the orientation of the disposable diapers at regularly spaced intervals.

The method in accordance with the present invention forms a package, including the following steps of transporting disposable diapers in a consecutive manner to a folding unit; folding each disposable diaper individually; changing the orientation of the disposable diapers at regularly spaced intervals; aligning a predetermined number of the disposable diapers with a diaper front face in a contacting relationship or a diaper back face in a contacting relationship to form an uncompressed array, wherein a predetermined number of the disposable diapers have an upper diaper section located in a first array region of the array, compressing the array; and placing the compressed array in a flexible outer casing.

A second predetermined number of the disposable diapers have an upper diaper section located in a second array region of the array.

The method in accordance with the present invention forms a package by transporting disposable diapers in a consecutive manner to a folding unit; folding each of the disposable diapers individually; changing the orientation of the disposable diapers at regularly spaced intervals; aligning a predetermined number of the disposable diapers with diaper front faces or diaper back faces in a contacting relationship to form an uncompressed array, wherein a predetermined number of the disposable diapers have an upper diaper section located in a first array region of the array and a second predetermined number of the disposable diapers have an upper diaper section located in a second array region of the array; compressing the array; placing the compressed array in a flexible outer casing; and wherein the compression force is substantially uniform across the first and second array regions.

What is claimed is:

1. A package containing an array of flexible articles, each said article having an article front face, an article back face, an article top face, an article bottom face, article side faces, an upper article section and a lower article section, said article sections having mutually different caliper; wherein a respective article front face is placed in contact with another article front face or wherein a respective article back face is placed in contact with another article back face; said array having a first array region and a second array region, said upper and lower article sections being distributed over said first and second array regions of said array, wherein said upper and lower article sections are distributed such that a reordered size difference of said first and second array regions is at least about 10% smaller than when all of said upper article sections are located in the same array region of said array.

2. A package according to claim 1, wherein said mutually different caliper of said article sections consists of a caliper in said upper article section different from said lower article section.

3. A package according to claim 1, wherein said package contains no compressing paper wrapping to maintain said array of said articles.

4. A package according to claim 1, wherein said upper and lower article sections of each said articles are distributed such that the sizes of said first and second array regions of said array are substantially equal.

5. A package according to claim 1, wherein each said article in contact with another article is placed with said article bottom faces in a contact with said top faces of adjacent articles forming a reoccurring pattern on opposite sides of said upper and lower article sections.

6. A package according to claim 1, wherein the reordered size difference is at least about 15% smaller.

7. A package according to claim 6, wherein the dimension of said first array region of said array is substantially equal to the dimension of said second array region of said array.

8. A package according to claim 7, wherein said mutually different caliper of said article sections consists of a caliper in said upper article section different from said lower article section.

9. A package comprising a flexible outer casing containing an array of compressed, flexible absorbent articles, each said article comprising an article front face, an article back face, an article top face, an article bottom face, article side faces, an upper article section and a lower article section, said article sections having mutually different compressibilities and calipers; wherein at least a portion of said absorbent articles are placed with said article front faces in a contacting relationship and at least a portion of said absorbent articles are placed with said article back faces in a contacting relationship; said array having a first array region and a second array region and said upper and lower article sections of each said articles being distributed over said first and second array regions of said array; wherein said distribution of said upper and lower article sections is such that the difference in the compression force for compression of said first and second array regions to between 0% and 90% of an uncompressed volume is at least 10% smaller than the difference in the compression force for compression of said first and second array regions when all of said upper article sections of each said articles are located in the same array region of said array; and said flexible outer casing maintains said array of compressed articles.

10. A package according to claim 9, wherein said upper and lower article sections of each said articles are distributed in such a way that the compression forces for said first and second array regions of said array are substantially equal.

11. A package according to claim 9, wherein at least a portion of each said articles is placed with said article bottom faces in a contacting relationship forming a reoccurring stack pattern with said article top faces of adjacent articles.

12. A package according to claim 11, wherein after compression the dimension along the direction of compression of said first array region of said array is equal to the dimension along the direction of compression of said second array region of said array.

13. A package according to claim 12, wherein after compression the expansion force of said first array region is equal to the expansion force of said second array region.

14. A package according to claim 13, wherein said absorbent articles consist of different caliper in said upper and lower article sections.

15. A package according to claim 12, wherein said absorbent articles consist of different caliper in said upper and lower article sections.

16. A package according to claim 9, wherein the orientation of each said articles is periodically alternated.

17. A package comprising an array of disposable diapers, said disposable diapers comprising a diaper front face, a diaper back face, a diaper top face, a diaper bottom face, diaper side faces, an upper diaper section and a lower diaper section, said diaper sections having mutually different calipers, wherein at least a portion of said disposable diapers are placed with said diaper front faces in a contacting relationship and at least a portion of said diaper back faces in a contacting relationship; further comprising a flexible outer casing; said array having a first array region and a second array region and said upper and lower diaper sections of said disposable diapers being distributed over said first and second array regions of said array, wherein said distribution of upper and lower diaper sections is such that the difference in size of said first and second array regions is at least about 10% smaller than when all of said upper diaper sections of said absorbent disposable diapers are located in the same array region of said array.

18. A package according to claim 17, wherein said upper and lower diaper sections of said disposable diapers are distributed such that the sizes of said first and second array regions of said array are substantially equal.

19. A package according to claim 18, wherein at least a portion of said disposable diapers are placed with said diaper bottom faces in a contacting relationship forming a reoccurring stack pattern with said top faces of adjacent disposable diapers.

20. A package according to claim 19, wherein the dimensions of said first array region of said array are equal to the dimensions of said second array region of said array.

21. A package according to claim 20, wherein said disposable diapers consist of different calipers in said upper and lower diaper sections.

22. A package according to claim 21, wherein said package does not contain compressing wrapping to maintain said array of said disposable diapers.

23. A package according to claim 18, wherein the orientation of said disposable diapers is periodically alternated.

24. A package containing an array of compressed, flexible disposable diapers, said disposable diapers comprising a diaper front face, a diaper back face, a diaper top face, a diaper bottom face, diaper side faces, an upper diaper section and a lower diaper section, said diaper sections having mutually different compressibilities and calipers; wherein at least a portion of said disposable diapers are placed with said disposable front faces in contacting relationship and at least a portion of said diaper back faces in contacting relationship; further comprising a flexible outer casing; said array having a first array region and a second array region and said upper and lower diaper sections of said disposable diapers being distributed over said first and second array regions of said array, wherein said distribution of said upper and lower diaper sections is such that the difference in the compression force for compression of said first and second array regions to between 0% and 90% of an uncompressed volume is at least 10% smaller than the force for compression of said first and second array regions when all of said upper diaper sections of said disposable diapers are located in the same array region of said array; and said flexible outer casing maintains said array of said compressed disposable diapers.

25. A package according to claim 24, wherein said upper and lower diaper sections of said disposable diapers are distributed in such a way that the compression forces for said first and second array regions of said array are substantially equal.

26. A package according to claim 24, wherein at least a portion of said disposable diapers are placed with said diaper bottom faces in adjacent contacting relationship forming a reoccurring stack pattern with said top faces of adjacent disposable diapers.

27. A package according to claim 26, wherein after compression the dimension along the direction of compression of said first array region of said array is equal to the dimension along the direction of compression of said second array region of said array.

28. A package according to claim 27, wherein after compression the expansion force of said first array region is equal to the expansion force of said second array region.

29. A package according to claim 28, wherein said disposable diapers consist of different calipers in said upper and lower diaper sections.

30. A package according to claim 29, wherein said package does not contain compressing wrapping to maintain said array of said compressed disposable diapers.

31. A package according to claim 24, wherein the orientation of said disposable diapers is periodically alternated.

* * * * *